United States Patent [19]
Sharpe et al.

[11] Patent Number: 5,574,041
[45] Date of Patent: *Nov. 12, 1996

[54] USE OF SPIPERONE DERIVATIVES AS IMMUNOSUPPRESSANT AGENTS

[75] Inventors: Richard J. Sharpe, Newtonville; Kenneth A. Arndt, Newton Centre; Stephen J. Galli, Winchester; Peter C. Meltzer, Lexington; Raj K. Razdan, Belmont; Howard P. Sard, Arlington, all of Mass.

[73] Assignee: Beth Israel Hospital Association, Boston, Mass.

[ * ] Notice: The term of this patent shall not extend beyond the expiration date of Pat. No. 5,290,783.

[21] Appl. No.: 893,534

[22] Filed: Jun. 4, 1992

Related U.S. Application Data

[63] Continuation-in-part of Ser. No. 815,283, Dec. 27, 1991, Pat. No. 5,290,783, which is a continuation-in-part of Ser. No. 494,740, Mar. 16, 1990, abandoned.

[51] Int. Cl.$^6$ ..................... A61K 31/445; A61K 31/415
[52] U.S. Cl. ............................. 514/278; 514/885
[58] Field of Search ..................... 514/278, 885

[56] References Cited

U.S. PATENT DOCUMENTS

| | | | |
|---|---|---|---|
| 2,788,309 | 4/1957 | Cooper et al. | 167/67 |
| 2,854,380 | 9/1958 | Jensen et al. | 167/67 |
| 3,155,670 | 11/1964 | Janssen et al. | 260/294 |
| 3,238,216 | 3/1966 | Janssen | 260/293.4 |
| 3,922,266 | 11/1975 | Katsube et al. | 260/240 |
| 3,996,363 | 12/1976 | Wade et al. | 424/258 |
| 4,228,287 | 10/1980 | van der Stelt | 546/236 |
| 4,555,504 | 11/1985 | Jones | 514/26 |
| 4,665,075 | 5/1987 | Vandenberk et al. | 514/259 |
| 4,839,342 | 6/1989 | Kaswan | 514/11 |
| 4,874,766 | 10/1989 | Ooms et al. | 514/258 |
| 4,937,249 | 6/1990 | Antoku et al. | 514/321 |
| 5,137,894 | 8/1992 | New et al. | 514/301 |
| 5,244,902 | 9/1993 | Sharpe et al. | 514/278 |
| 5,290,783 | 3/1994 | Sharpe et al. | 514/278 |

FOREIGN PATENT DOCUMENTS

| | | |
|---|---|---|
| 633914 | 12/1963 | Belgium . |
| 2654934 | 11/1989 | France . |
| WO9102527 | 3/1991 | WIPO . |
| WO91/13622 | 9/1991 | WIPO . |

OTHER PUBLICATIONS

Akamatsu, et al., "J. Investigative Dermatology." vol. 95, pp. 271–274 (1990).
Ameisen, et al., "A New Interpretation of The Involvement of Serotonin in Delayed–Type Hypersensitivity" *The Journal of Immunology* vol. 142 (9), pp. 3171–3179 (1989).
Blozovski, et al., "Action de la Sérotonine de la Réserpine et D'Autres Agents Pharmacologiques sur la Sécrétion Sudorale. Études Hygrophotographiques" Arch. Int. Pharmacodyn. vol. 123, pp. 58–66 (1959).
"Chemical Abstracts" vol. 54, Abstract 215049–1.
Burka, et al., "Dopaminergic (Co–Mediator) Modulation of Release of Histamine and SRS–A in the Calf." *British Journal of Pharmacology* vol. 58 (3), p. 445 (1976).
Coffman, "The Attenuation by Reserpine or Guanethidine of the Cutaneous Vasoconstriction Caused by Tobacco Smoking", *American Heart Journal* vol. 74 (2), pp. 229–234 (1967) *Chemical Abstracts* vol. 67, p. 7624 81019W (1967).
Diezel, et al., "Inhibition of Cutaneous Contact Hypersensitivity by Calcium Transport Inhibitors Lanthanum and Diltiazem" *The Journal for Investigative Dermatology* vol. 93, pp. 322–325 (1989).
Eyre, "Dopamine Potentiates Anaphylactic Contraction of Pulmonary Vein of Calf." *Research Communication in Chemical Pathology and Pharmacology* vol. 22(3) pp. 447–453 (1978).
Fanta, "Calcium–Channel Blockers in Prophylaxis and Treatment of Asthma" *The American Journal of Cardiology* vol. 55, pp. 202B–209B (1985).
Hellstrand, et al., "Role of Serotonin in the Regulation of Human Natural Killer Cell Cytotoxicity" *The Journal of Immunology* vol. 139 (3), pp. 869–875 (1987).
Kligman, "The Comparitive Histopathology of Male–Pattern Baldness and Senescent Baldness" *Clinics In Dermatology.* pp. 108–118 (Oct. 1988).
Leysen, et al., "Receptor Binding of R 41 468, A Novel Antagonist at 5–HT$_2$ Receptors." *Life Sciences* vol. 28(9), pp. 1015–1022 (1981).
Loffman, et al., "American Heart Journal" vol. 74(2), pp. 229–234, (1967).
"Chemical Abstracts" vol. 67, (1967), Abstract 81019W.
Login, et al., "Reserpine is a Calcium Channel Antagonist in Normal and GH$_3$ Rat Pituitary Cells" *American Journal of Physiology* vol. 248, pp. E15–E19 (Jan. 1985).
Moerlein, et al., "Effect of Lipophilicity on the In Vivo Localization of Radiolabelled Spiperone Analogues", *Int. J. Nucl. Med. Biol,* vol. 12, No. 5, pp. 353–356 (1985).
Mekori, et al., "Studies of the Role of Mast Cells in Contact Sensitivity Responses Passive Transfer of the Reaction into Mast Cell–Deficient Mice Locally Reconstituted with Cultured Mast Cells: Effect of Reserpine on Transfer of the Reaction with DNP–Specific Cloned T Cells" *Cellular Immunology* vol. 109, pp. 39–52 (1987).
Nakanishi, et al., "Spirohydantoin Derivatives", *Chemical Abstracts,* Vo. 75, p. 437 (1971), Abstract 110315n.

(List continued on next page.)

Primary Examiner—Allen J. Robinson
Assistant Examiner—Mary C. Cebulak
Attorney, Agent, or Firm—Cheryl K. Zalesky; Kilpatrick & Cody

[57] ABSTRACT

A method for suppressing an immune response in a mammal by treating the mammal with an effective amount of spiperone derivative that is without significant neuroleptic effect due to decreased binding to serotonin and/or dopamine receptors as compared with unmodified or uncomplexed spiperone, or due to topical application which maximizes local immunosuppression while limiting systemic absorption and neuroleptic effects. The spiperone derivatives are capable of inhibiting classic contact hypersensitivity reactions.

38 Claims, 9 Drawing Sheets

OTHER PUBLICATIONS

Schroeder, et al., "Transient Absence of C5a–Specific Neutrophil Function in Inflammatory Disorders of the Skin*" *J. Investigative Dermatology* vol. 85, pp. 194–198 (1985).

Sharpe, et al., "Inhibition of Cutaneous Contact Hypersensitivity in the Mouse with Systemic or Topical Spiperone: Topical Application of Spiperone Produces Local Immunosuppression without Inducing Systemic Neuroleptic Effects" *J. Investigative Dermatology* vol. 99(5), pp. 594–600 (1992).

Sternberg, et al., "Effect of Serotonin on Murine Macrophages: Suppression of Ia Expression by Serotonin and its Reversal by 5–HT$_2$ Serotonergic Receptor Antagonists" *J. Immunology* vol. 137(1), pp. 276–281 (1986) *Fed. Proc.* vol. 44(5), p. 7526 (1985).

Sternberg, et al., "Macrophage Activation by Serotonin (5–HT) is Affected by Interferon $\gamma$ (IFN$\gamma$) Concentration and is antagonized by Spiperone and Ketanserin," *Federation Proceedings,* Abstracts, 44(5):7526 (1985).

Tucker, et al., "Inflammation in Acne Vulgaris: Leukocyte Attraction and Cytotoxicity by Comedonal Material" *Investigative Dermatology* vol. 74, pp. 21–25 (1980).

Reynolds, "Martindale, The Extra Pharmacopoeia," The Pharmaceutical Press, 1989.

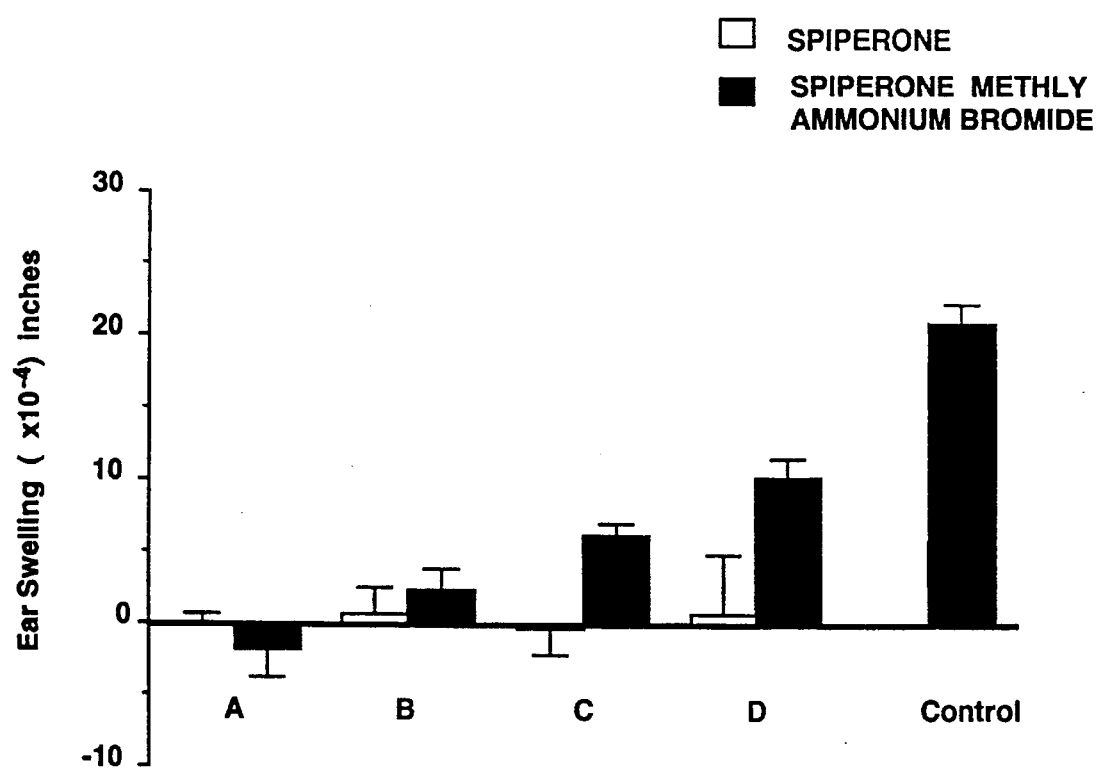
FIGURE:11

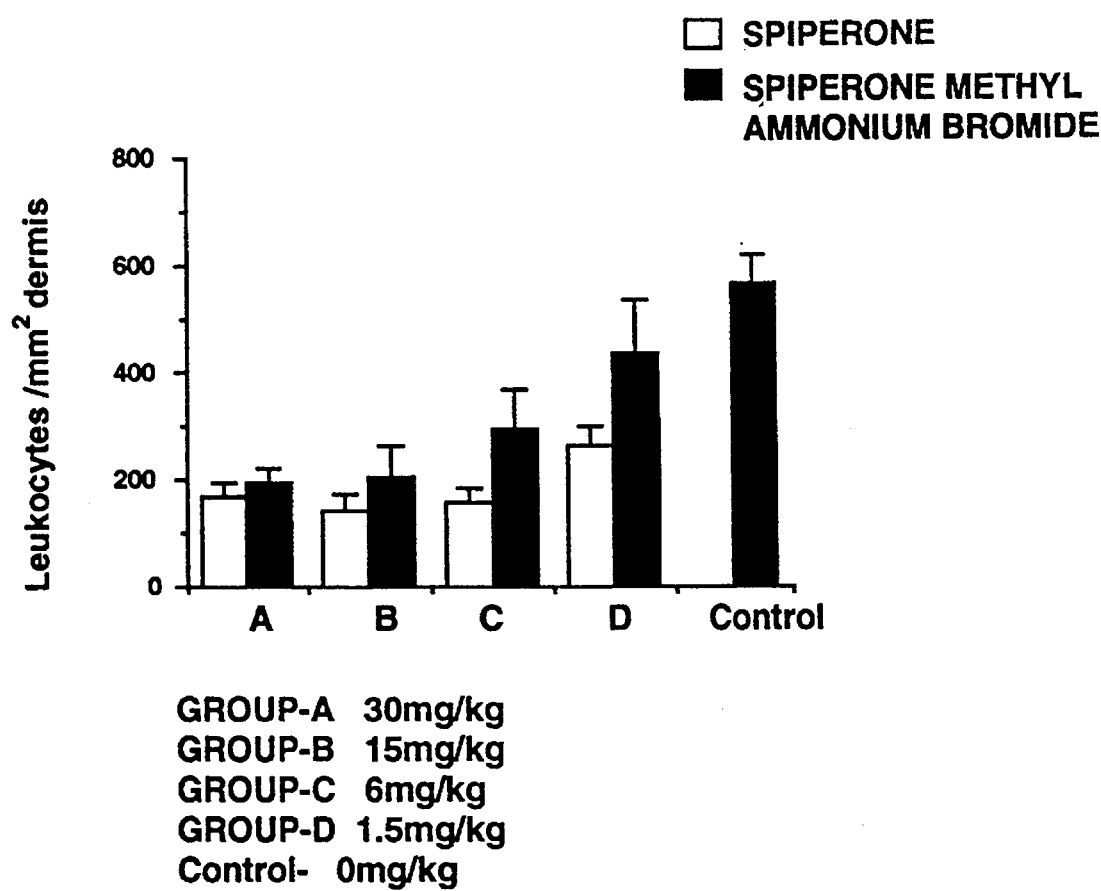
FIGURE:12

USE OF SPIPERONE DERIVATIVES AS IMMUNOSUPPRESSANT AGENTS

This application is a continuation-in-part of U.S. Ser. No. 07/815,283, filed on Dec. 27, 1991, now U.S. Pat. No. 5,290,783, that is a continuation-in-part of U.S. Ser. No. 07/494,740, filed on Mar. 16, 1990, now abandoned.

BACKGROUND OF THE INVENTION

This invention is in the field of the suppression of immune responses, and in particular relates to a method for the treatment of immune disorders that preferably includes administering a spiperone derivative that does not have a significant neuroleptic effect or is administered in a way that minimizes its neuroleptic effects.

The immune system specifically recognizes and selectively eliminates foreign invaders, or other antigenic agents, by a process known as the immune response. The immune response has three major characteristics: it responds adaptively to foreign invaders, it exhibits strong specificity, and it displays a long-term memory of earlier contacts with specific foreign pathogens or antigens. The immune response involves the production of antibody and/or the destruction of antigenic cells by lymphocytes, which are highly specific for the antigen or hapten.

Cutaneous contact hypersensitivity responses are complex expressions of cellular immunity characterized by antigen-dependent changes in lymphocyte traffic, and alterations in vascular permeability and blood flow. While T cells are required for the expression and immunological specificity of the response, many other cell types also have roles in the reaction, including Langerhans' cells, keratinocytes, and vascular endothelial cells. Antigen presentation is thought to be effected primarily by Langerhans' cells, whereas much of the local expression of the response is thought to be regulated by cytokines derived from both T cells and accessory cells.

Pharmacological studies have indicated that a number of mediators in addition to cytokines may contribute to the expression of contact hypersensitivity and other forms of cell-mediated immunity. There has been particular interest in the role of serotonin (5-hydroxytryptamine, 5-HT) in these reactions. For example, serotonin has been shown to have a wide range of actions on T cells and other effector cells in vitro or in vivo, and pharmacological agents that deplete or antagonize serotonin can diminish expression of cell-mediated immunity. Early studies raised the possibility that such agents might reduce cell-mediated immunity by antagonizing or depleting mast cell-associated serotonin. However, more recent findings indicate that at least one of these drugs, reserpine, can inhibit contact hypersensitivity independently of mast cells, probably through direct effects on T cells.

Although contact hypersensitivity represents a classical example of an immune response, many pathogenic conditions in mammals are solely or in part the result of immune responses. Examples of other pathogenic or undesired immune responses include host rejection of foreign organ or tissue transplants; graft-vs-host disease in which donor immunological cells present in the graft attack host tissues in the recipient of the graft; diseases with proven or possible autoimmune components, such as rheumatoid arthritis, juvenile rheumatoid arthritis, psoriatic arthritis, psoriasis, leprosy reversal reactions, erythema nodosum leprosum, autoimmune uveitis, multiple sclerosis, allergic encephalomyelitis, systemic lupus erythematosis, acute necrotizing hemorrhagic encephalopathy, idiopathic bilateral progressive sensorineural hearing loss, aplastic anemia, pure red cell anemia, idiopathic thrombocytopenia, polychondritis, scleroderma, Wegener's granulomatosis, chronic active hepatitis, myasthenia gravis, Stevens-Johnson syndrome, idiopathic sprue, lichen planus, Crohn's disease, Graves ophthalmopathy, sarcoidosis, primary biliary cirrhosis, primary juvenile diabetes, dry eye associated with Sjögren's syndrome, uveitis posterior, and interstitial lung fibrosis; allergic asthma; and inappropriate allergic responses to environmental stimuli such as poison ivy, pollen, insect stings and certain foods, including atopic dermatitis and contact dermatitis.

Various therapeutics that have been utilized as immunosuppressants include steroid hormones, anti-metabolites such as methotrexate and azathioprine, cyclosporine, alkylating agents such as cyclophosphamide and busulfan, and certain antibiotics. However, there still remains a strong need to provide new immunosuppressive agents that minimize or prevent these pathogenic immune responses.

In contrast to the immune response, an inflammatory response is a pathologic condition that can occur in response to immunologically non-specific injury, either from physical (such as trauma), chemical, or biologic agents. An inflammatory response is characterized by increased blood flow and redness in the inflamed area, increased capillary permeability and edema, and recruitment of immunologically non-specific white blood cells, especially neutrophils, that remove injurious material and promote repair. Unlike immune responses, inflammatory responses do not respond adaptively to the inciting stimulus, do not show specificity and do not exhibit long term memory.

Cellular products of lymphocytes may contribute to or induce an inflammatory response. However, because of the differences in mechanisms, a compound can function as an antiinflammatory agent without having immunosuppressive properties. Phenylbutazone, indomethacin, aspirin, ibruprofen, and acetaminophen are examples of antiinflammatory compounds which have no significant immunosuppressive activity, as demonstrated by their lack of a significant effect on immunological mediated responses, such as contact hypersensitivity.

Spiperone (8-[3-{p-fluorobenzoyl}propyl]-1-propyl]-1-phenyl-1,3,8-triazaspiro-[4.5]decan-4-one) is a neuroleptic agent with central nervous system (CNS) dopamine and serotonin (5-HT) receptor antagonist properties. Some analogues of spiperone are useful as experimental reagents in dopamine and serotonin receptor studies. For example, the high affinity of an immobilized spiperone derivative, 3-(2-Aminoethyl)-8-[3-(4-fluorobenzoyl)propyl]-4-oxo-1-phenyl-1,3,8-triazaspiro[4.5]decan-4-one trihydrochloride, for dopamine receptors has made it possible to isolate these receptors in pure form. Radiopharmaceuticals based on spiperone and its analogues have been shown to be useful in assessing dopamine receptor function based on positron emission tomography (PET) in animals and man. Spiperone has also been shown to bind to human and mouse lymphocytes, although the mechanism responsible for such binding is uncertain.

There remains a need for compounds that are immunosuppressants but do not exhibit significant neuroleptic activity.

It is therefore an object of the present invention to provide a method and compositions for suppressing pathogenic immune responses.

It is another object of the present invention to provide a method and compositions for suppressing pathogenic immune responses that is without significant neuroleptic effect.

SUMMARY OF THE INVENTION

A method for treating a human or other mammal in need of immunosuppression is disclosed wherein the mammal is administered an effective amount of a spiperone derivative that does not have a significant neuroleptic effect, in a pharmaceutically-acceptable diluent or carrier for systemic or topical application.

Although the parent spiperone has a strong neuroleptic effect when administered systemically (but not when administered topically), it is used in the examples as a model of an active immunosuppressant. Other compounds with a spiperone nucleus, but without the neuroleptic activity, can be measured against this model, and are considered to be immunosuppressants if they suppress the leukocyte infiltrate and/or the ear swelling associated with an experimental contact hypersensitivity response by at least 40% at 24 hours after specific antigen challenge.

In the preferred method of administration, the spiperone derivatives are administered systemically, for example, by injection, in a pharmaceutical carrier such as saline, in an amount effective to immunosuppress the patient. In a second embodiment, the derivatives are administered topically in a suitable carrier to effectively immunosuppress the patient at the site of application, without producing a significant neuroleptic effect. Other pharmaceutical compositions include a spiperone derivative combined with a cycloamylose, such as cyclodextrin, which can used to modify the pharmokinetics of the compound.

BRIEF DESCRIPTION OF THE FIGURES

In FIG. 8a, the slight effect of treatment of the right ears with spiperone on reactions expressed in the left ears of the same mice was not significant (p>0.05).

FIG. 11—Comparative effects of varying doses of systematically administered spiperone methyl quaternary ammonium bromide salt versus spiperone on tissue swelling associated with oxazalone-induced cutaneous contact hypersensitivity reactions. Spiperone or spiperone methyl quaternary ammonium bromide salt were administered to Balb/c mice 1 hour after challenge for contact hypersensitivity. The change in ear thickness (post-challenge value minus baseline pre-challenge value) was measured 24 hours after oxazalone challenge. The data is presented as the mean ±SEM. The reduction in ear swelling observed with spiperone and spiperone methyl quaternary ammonium bromide salt was significant when compared to the reactions observed in the control, vehicle treated animals at all dosage levels (30 mg/kg, 15 mg/kg, 6 mg/kg, and 1.5 mg/kg, all given intraperitoneally in 10% DMSO, 90% water).

FIG. 12—Comparative effects of systemic treatment (intraperitoneal) with vehicle (0 mg/kg) or varying doses of spiperone or spiperone methyl quaternary ammonium bromide salt on leukocyte infiltration associated with 24-hour contact hypersensitivity reactions. The data (mean ±SEM) are derived from the same mice whose ear thickness values are shown in FIG. 11. The reduction in leukocyte infiltration observed in animals treated with 30 mg/kg, 15 mg/kg, 6 mg/kg and 1.5 mg/kg of spiperone was significant when compared to the reactions observed in animals treated with vehicle alone (P<=0.05). Doses of 30 mg/kg, 15 mg/kg and 6 mg/kg of spiperone methyl quaternary ammonium bromide salt resulted in significant suppression of leukocyte infiltration.

DETAILED DESCRIPTION OF THE INVENTION

Definitions

Figure 1:
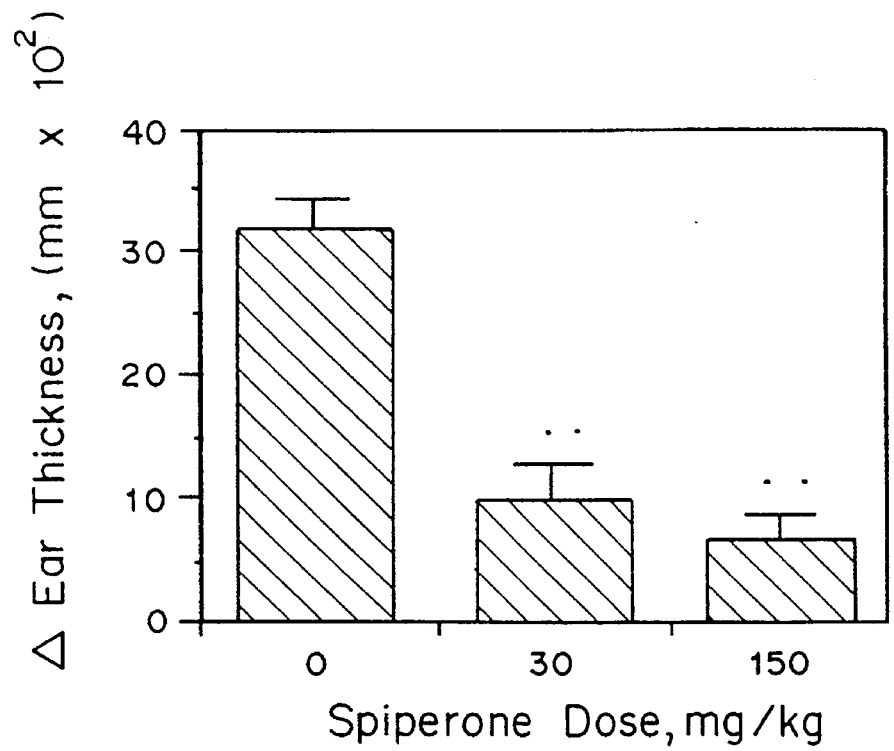
FIG. 1—Effect of systemic spiperone (30 or 150 mg/kg, subcutaneously) on the tissue swelling associated with oxazolone-induced cutaneous contact hypersensitivity reactions. Spiperone or vehicle alone (0) was administered to C57BL/6J mice 1 hour after challenge for contact hypersensitivity. The change in ear thickness (post-challenge value minus baseline pre-challenge value) was measured 24 hours after oxazolone challenge. The data are presented as the mean ±SEM (standard error of the mean). The reduction in ear swelling observed with either 30 or 150 mg/kg spiperone was significant when compared to the reactions observed in the control animals (**=$p<0.01$).

The term alkyl, as used herein, unless otherwise specified, refers to a saturated straight, branched, or cyclic hydrocarbon of $C_1$ to $C_{20}$, including methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term aryl, as used herein, and unless otherwise specified, refers to phenyl or substituted phenyl, wherein the substituent is independently halo, alkyl, or oxy(alkyl) (for example, methyoxy, ethoxy, etc.), and wherein the aryl can have up to three substituents.

Spiperone Derivatives

As used herein, spiperone derivatives without significant neuroleptic effect are identified by their ability to inhibit or prevent cutaneous contact hypersensitivity, as described in detail in Example 1. Other methods can also be used to identify these compounds, including animal models of allograft rejection, experimental allergic encephalomyelitis, lupus erythematosus, Freund's adjuvant arthritis and/or graft versus host disease. Measurement of their ability to bind to serotonin or dopamine receptors can be carried out as described in detail in Example 3, or by their lack of ability to act as a tranquilizer or neuroleptic in mammals, for example, by demonstrating that they are no different than placebo in the hot plate test of Eddy, et al., *J. Pharmacol.* 107:385 (1953) and 110:135 (1954).

The chemically unrelated serotonin receptor antagonists, trazadone and mianserin, and the dopamine receptor antagonist, haloperidol, are not effective in suppressing contact hypersensitivity. On this basis, it is clear that the mechanism of action of spiperone and spiperone derivatives in suppressing the immune response is independent of their serotonin or dopamine receptor blocking properties. Therefore, spiperone derivatives with immunosuppressive effect yet without neuroleptic effect can be provided by the method of selection disclosed generally herein.

As used herein, the term "spiperone derivative" refers to a molecule (1) that contains the spiperone nucleus:

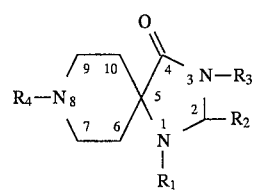

(2) does not have significant neuroleptic effect, as measured using the assay set out in Example 3; and (3) exhibits an immunosuppressive effect when provided systemically or topically, as measured using the assay set out in Example 1, or as evaluated in vivo in humans by the agent's ability to inhibit contact hypersensitivity responses to patch test allergens in patients hypersensitive to a given allergen.

I. Structure and Synthesis of Spiperone Derivatives

The parent spiperone is 8-[3-(p-fluorobenzoyl)propyl]-1-phenyl-1,3,8-triazaspiro[4.5]decan-4-one, which has the structure illustrated below.

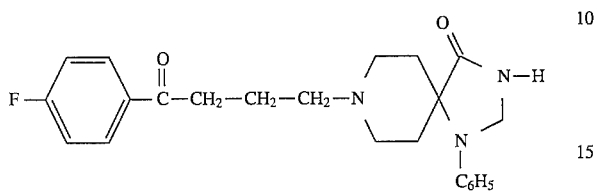

As demonstrated in Example 1, the parent spiperone has significant immunosuppressive activity. However, uncomplexed or unmodified spiperone also has significant neuroleptic effect when administered systemically. However, spiperone can be complexed, or chemically modified without undue experimentation using methods known to those skilled in the art, to retain its immunosuppressive activity and eliminate the undesired neuroleptic effect by decreasing the ability of the compound to bind to dopamine or serotonin receptors. Alternatively, Example 1 shows that spiperone can be given topically to produce local immunosuppression without inducing a significant neuroleptic effect.

Compounds containing the spiperone nucleus, and methods of synthesis thereof, are disclosed in U.S. Pat. Nos. 3,155,669; 3,155,670; 3,161,644; and 3,238,216; all of which are hereby incorporated by reference. The spiperone derivatives disclosed herein can be made according to known procedures, for example as disclosed in the patents identified herein, or by obvious modifications of known procedures. The compounds containing the spiperone nucleus can be complexed, or chemically modified, if necessary, to retain immunosuppressive activity and prevent the undesired neuroleptic effect.

Other compounds that contain the spiperone nucleus, and which can be complexed or chemically modified if necessary to prevent a neuroleptic effect, are of the formula:

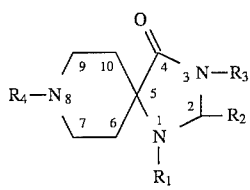

wherein:

$R_1$=H; alkyl, specifically including $CH_3-$, cyclohexyl, $(CH_3)_2CH-$, $CH_3(CH_2)_3-$, $(CH_3)_2CHCH_2-$, $CH_3CH_2CH(CH_3)-$, $(CH_3)_3C-$, and $-CH_3(CH_2)p$; $Y-CH_2(CH_2)_n$ — or $Ar_1$, specifically including $C_6H_5-$, (2, 3, or 4)-$(OCH_3)C_6H_4-$ and (2, 3, or 4)-$(CH_3)C_6H_4-$; 2—X—$C_6H_4-$, 3—X—$C_6H_4-$, or 4—X—$C_6H_4-$;

$R_2$=H or $C_1$ to $C_{20}$ alkyl;

$R_3$=H; alkyl, specifically including $-CH_3$, $CH_3CH_2-$, $CH_3CH_2CH_2-$, $(CH_3)_2CH-$, or $CH_3(CH_2)_n-$; $CN(CH_2)_2-$; X—$(CH_2)_n-$; X—$(CH_2)_nCO-$; $NH_2C(NH)NHC(NH)(aryl)(CH_2)_n-$; or X—(aryl)-$(CH_2)_n-$;

$R_4$=H, $C_6H_5CH(CH_2CH_3)CH_2-$, $C_6H_5CH(CH_3)(CH_2)_2-$, $C_6H_5CH_2CH(CH_3)CH_2-$, $C_6H_5CH_2CH_2CH(CH_3)-$, $C_6H_5CH(CH_3)(CH_2)_3-$, (2, 3, or 4)-(alkyl)—$C_6H_4CH(CH_3)(CH_2)_3-$, (2, 3, or 4)-(alkyloxy)—$C_6H_4CH(CH_3)(CH_2)_3$, (2, 3, or 4)—X—$C_6H_4$-alkyl, specifically including (2, 3, or 4)—X—$C_6H_4CH(CH_2CH_3)CH_2-$, (2, 3, or 4)—X—$C_6H_4CH(CH_3)$ $(CH_2)-$ 4—X—$C_6H_4CH(CH_3)$ $(CH_2)_2-$, and 4—X—$C_6H_4$—CH $(CH_3)$ $(CH_2)_3-$; $C_6H_5CH(OCH_3)$ $(CH_2)_2-$,

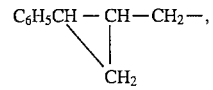

$C_6H_5CO(CH_2)_3-$, $C_6H_5CO(CH_2)_4-$, (2, 3, or 4)-(alkyl)-$C_6H_4CO(CH_2)_3-$, (2, 3, or 4)-(alkyl-oxy)—$C_6H_4CO(CH_2)_3-$, (2, 3, or 4)—X—$C_6H_4CO(CH_2)_n-$, 2-thienyl—CO—$(CH_2)_3-$,

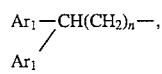

(2, 3, or 4)—X—$C_6H_4C(CH_3)CH(CH_2)_2-$, where the conformation about the double bond is cis or trans,
(2, 3, or 4)—X—$C_6H_4C(CH_3)CHCH_2-$, where the conformation about the double bond is cis or trans,
(2, 3, or 4)—X—$C_6H_4COCH=CHCH_2-$,
$Y-CH_2(CH_2)_n-$, $Ar_1-(CH_2)_n-$, $C_1$ to $C_{20}$ alkyl, X—$(CH_2)_nCO-$, or X—$(CH_2)_n-$;

n=1 to 6;

p is 1 to 20;

X= is independently F, Cl, Br, I, $OCH_3$, $SO_3^{31}$, $NH_2$, H, —OH, —COOH, —COOR, —$SO_3H$, —CN, —$NHSO_3H$, —$NO_2$, or —$SO_2NH_2$;

Y=H, F, Cl, Br, I, —$SO_3^=$, —$PO_4^=$, —OH, —SH, —$SCH_3$, —$CH_3SO_2^-$, —$NH_2$, or —$CO_2^-$; and $Ar_1$ is, independently, aryl, (2, 3, or 4—X—$C_6H_4-$), (2, 3, or 4)-$(CH_2X)C_6H_4-$, (2, 3, or 4)-$(CX_3)C_6H_4-$, (2, 3, or 4)-$(CHX_2)C_6H_4-$, 2-thienyl, or (2, 3, or 4)—X—$C_6H_4CH_2-$;

or its pharmaceutically acceptable salt, including any quaternary salt known by those in the art, and specifically including the quaternary ammonium salt of the formula —$NR^+Z^-$, wherein R is alkyl or benzyl, and Z is a counteranion, including chloride, bromide, iodide, —O-alkyl, toluenesulfonate, methylsulfonate, sulfonate, phosphate, or carboxylate (such as benzoate, succinate, acetate, glycolate, propionate, succinate, maleate, malate, citrate, tartrate, ascorbate, benzoate, cinnamoate, mandeloate, benzyloate, and diphenylacetate).

Those forms of spiperone that are particularly useful in the method are those in which $R_1$ through $R_4$ are chosen to minimize neuroleptic activity and to maximize immunosuppressant activity of the molecule, or when the spiperone is in the form of a quaternary salt.

The potential utility of any one of the above-described forms of spiperone to act as an immunosuppressant can be conveniently determined by synthesizing the compound and testing it in the biological assay described in Example 1. Also, the neuroleptic activity of the spiperone derivatives can be estimated as described in Example 3.

II. Complexation or Modification of the Spiperone Nucleus to Prevent Significant Neuroleptic Effect As discussed above, immunosuppressive compounds with a spiperone nucleus that have a neuroleptic effect can be complexed or modified to eliminate that effect, by one or more of the following processes.

A. Decreasing the Lipophilicity, Equivalent to Increasing the Hydrophilicity of the Compound Compounds with a spiperone nucleus that exhibit an immunosuppressive effect yet also exhibit a neuroleptic effect can be modified to minimize the neuroleptic effect by decreasing the lipophilicity (equivalent to increasing the hydrophilicity) of the molecule. This can be done by adding one or more charged side chain(s) onto the molecule or by altering the existing side chain to make it more polar. The hydrophilicity of spiperone derivatives will in general increase when charged substituents are added.

For example:

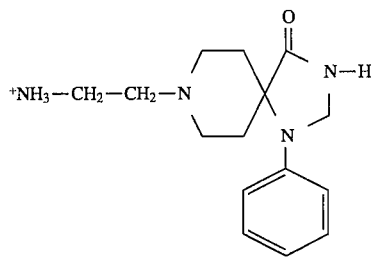

would be expected to be much more hydrophilic than the parent compound.

Moerlein et al. (*Int. J. Nucl. Med. Biol.* 12:353–356, 1985) have synthesized a number of forms of spiperone designed to increase the lipophilicity of the compound, and its potential ability to cross the blood-brain barrier, where they interact with dopamine and serotonin receptors.

B. Increasing the Size of the Molecule

Another technique for reducing the central nervous system (CNS) effects of compounds that contains a spiperone nucleus is to increase the size of the molecule via a covalent linkage to a large moiety (e.g., albumin or polyethylene glycol), using standard techniques of organic synthesis or by choosing a spiperone derivative with large substitutions ($R_1$, $R_2$, $R_3$, or $R_4$).

C. Complexing the Compound with Spiperone Nucleus with a Cyclic Molecule

A fourth method for reducing the central nervous system (CNS) effects of a compound that contains a spiperone nucleus includes forming a non-covalent complex of the compound with a cyclic molecule such as a cycloamylose (e.g., a cyclodextrin such as β-cyclodextrin), which has a spatial arrangement of hydroxyl groups whereby the outer surface of the ring formed by the cycloamylose is hydrophilic and the inner surface is lipophilic. When utilized in aqueous solution, this structure permits molecules (or parts thereof), termed "guest molecules", which are less polar than water and which are of suitable dimensions, to be incorporated into the lipophilic inner cavity, such that the cycloamylose/guest molecule complex presents to the blood-brain barrier as a relatively large and polar compound which is unable to penetrate the barrier. Such complexes may be prepared by any method known to the art, including those described in U.S. Pat. No. 4,555,504, which discloses β-cyclodextrin complexed with digoxin.

Spiperone altered or complexed by any of the above methods (with the effect of reducing the CNS effects of the compound to an acceptable level), and which exhibits the ability to suppress an immune response, is referred to herein as "a spiperone derivative without significant neuroleptic effect." The efficacy of any such spiperone entity as an immunosuppressant can be tested in the assay described in Example 1 below. Whether the same entity is capable of inducing the neuropharmacological side effects observed for spiperone can be assayed by, for example, the hot plate test of Eddy et al., *J. Pharmacol.* 107:385 (1953) and 110:135 (1954), or by the method of Example 3.

The central nervous system side effects of a spiperone derivative can be estimated using molecular modeling and/or pharmacophore analysis. The dopamine and serotonin receptors are well characterized and strategies for estimating binding of drugs to these receptors are well established. For example, Schmidt, et al., *Molecular Pharmacology* 38:511–516 (1990), describe an algorithm for estimating the binding affinity of drugs to the 5-HT receptor. Also, a composite pharmacophore analysis and chemical database screening strategy is described by Sleight, et al, *Naunyn-Schmiedebergs Arch. Pharmacol.* 343:109–116 (1991), and Schmidt, A. W. and Peroutka, S. J., *Mol. Pharmacol.* 36(4):505–511 (1989). $R_1$ through $R_4$ can be chosen to minimize serotonin and/or dopamine receptor binding using these or similar approaches and the derivatives can then be tested for immunosuppressive activity, as described in example 1.

D. Administration as a Quaternary Salt

Spiperone or its above-defined derivative can be administered in the form of a pharmaceutically acceptable quaternary salt. Quaternary salts are typically less lipophilic than the corresponding unquaternized compound, and therefore have a decreased effect on the central nervous system. Nonlimiting examples of quaternary salts that can be used include salts prepared from methyl chloride, methyl bromide, methyl iodide, methyl sulfate, methyl benzene-sulfonate, methyl p-toluenesulfonate, ethyl chloride, ethyl bromide, ethyl iodide, n-propyl chloride, n-propyl bromide, n-butyl bromide, isobutyl bromide, sec-butyl bromide, n-amyl bromide, n-hexyl chloride, benzyl chloride, benzyl bromide, and ethyl sulfate.

III. Therapeutic Compositions

Mammals, and specifically humans, suffering from pathogenic immune responses can be treated by administering to the patient an effective amount of the spiperone derivative or its salt in the presence of a pharmaceutically acceptable carrier or diluent.

The spiperone derivative is administered subcutaneously, intravenously, intraperitoneally, intramuscularly, parenterally, orally, submucosally, by inhalation, transdermally via a slow release patch, or topically, in an effective dosage range to cause immunosuppression. Typical systemic dosages for all of the herein described conditions are those ranging from 0.1 mg/kg to 500 mg/kg of body weight per day as a single daily dose or divided daily doses. Typical dosages for topical application are those ranging from 0.001 to 100% by weight of the active compound. In general, local immunosuppression can be achieved by administering topically lower doses of spiperone derivatives than would be required if the agents were administered systemically. The effective dosage of the parent compound, spiperone, for systemic immunosuppression is believed to be higher than the effective dosage of spiperone for inducing a neuroleptic effect.

The spiperone derivative is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound of the spiperone derivative in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The spiperone derivative or its salts can be administered as a component of an elixir, suspension, syrup, wafer, chewing gum or the like. A syrup may contain, in addition to the active compounds, sucrose as a sweetening agent and certain preservatives, dyes and colorings and flavors.

The spiperone derivative can also be mixed with other active materials which do not impair the desired action, or with materials that supplement the desired action, such as antibiotics, antifungals, antiinflammatories, antivirals, or other immunosuppressive agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If administered intravenously, preferred carriers are physiological saline, bacteriostatic water, Cremophor EL™ (BASF, Parsippany, N.J.) or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the spiperone derivative is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene. A number of solutions and ointments are commercially available, especially for ophthalmic applications.

Spiperone derivatives can be provided in the form of pharmaceutically-acceptable salts. As used herein, the term "pharmaceutically-acceptable salts or complexes" refers to salts or complexes that retain the desired biological activity of the parent compound and exhibit minimal, if any, undesired toxicological effects. Examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, and the like, or with an organic cation formed from N,N-dibenzylethylene-diamine or ethylenediamine; or (c) combinations of (a) and (b); e.g., a zinc tannate salt or the like.

IV. Immunosuppressant Activity of Spiperone Derivatives

Spiperone derivatives are capable of acting systemically or topically to suppress the immune response in animals. As such, the compounds, or therapeutic compositions thereof, are useful for the treatment of a myriad of immunological disorders. Examples of such disorders that are usually treated systemically include those related to host rejection of foreign organ or tissue transplants; graft-vs-host disease; and autoimmune diseases, such as rheumatoid arthritis, juvenile rheumatoid arthritis, psoriatic arthritis, psoriasis, autoimmune uveitis, multiple sclerosis, allergic encephalomyelitis, systemic lupus erythematosis, acute necrotizing hemorrhagic encephalopathy, idiopathic bilateral progressive sensorineural hearing loss, aplastic anemia, pure red cell anemia, idiopathic thrombocytopenia, polychondritis, scleroderma, Wegener's granulomatosis, chronic active hepatitis, myasthenia gravis, atopic dermatitis, Stevens-Johnson syndrome, idiopathic sprue, Crohn's disease, Graves ophthalmopathy, sarcoidosis, primary biliary cirrhosis, primary juvenile diabetes, uveitis posterior, and interstitial lung fibrosis; and allergic reactions, including atopic dermatitis and contact dermatitis. Examples of other immune disorders of the skin, mucosa, or eye that generally are treated topically (although many can also be treated systemically) include alopecia areata, arthropod bites, lichen planus, cutaneous lupus erythematosus, scleroderma, dry eye associated with Sjögren's syndrome, and drug reactions.

The compounds are specifically useful in the treatment of allograft rejection, for example, of heart, kidney, and lung tissue, and in the treatment of graft vs. host disease associated with bone marrow transplants.

The ability of the neuroleptic agent spiperone (8-[3-{p-fluorobenzoyl}propyl]-1-phenyl-1,3,8-triazaspiro-[4.5]decan-4-one) to influence the tissue swelling and leukocyte infiltration associated with contact hypersensitivity reactions in mice was evaluated as described in detail in Example 1. The parent spiperone compound was used for the procedure in Example 1 as a model of an active immunosuppressant. Other compounds with a spiperone nucleus can be measured against this model, and are considered active if they suppress the leukocyte infiltrate and/or the swelling response by at least 40% 24 hours after specific antigen challenge.

In the procedure of Example 1, contact hypersensitivity reactions were elicited by applying the haptens oxazolone or dinitrofluorobenzene topically to one or both ears five to eight days after epicutaneous sensitization. When spiperone was given subcutaneously at a dose of 150 mg/kg, 1 hour after challenge with oxazolone, cutaneous contact hypersensitivity to this hapten was almost totally abrogated. A dose of 40 or 30 mg/kg subcutaneously also significantly suppressed the reactions but to a lesser degree than the higher dose. When applied topically, preparations of spiperone significantly suppressed both the tissue swelling and the leukocyte infiltration associated with the elicitation phase of contact hypersensitivity to either oxazolone or dinitrofluorobenzene. Topical treatment with spiperone also suppressed the sensitization phase of contact sensitivity. However, mice treated topically with spiperone, unlike those treated systemically, exhibited no drowsiness or other evidence of central nervous system effects.

Spiperone expresses both serotonin and dopamine receptor antagonist activity. However, unlike spiperone, it was discovered that the chemically unrelated serotonin antagonists, trazadone and mianserin, and the dopamine receptor antagonist, haloperidol, were not effective in suppressing contact hypersensitivity. Additionally, the methyl quaternary ammonium bromide salt of spiperone has substantially reduced CNS activity, while retaining immunosuppressive activity. On the basis of this, it is clear that the mechanism of action of spiperone on the immune response is independent of its serotonin or dopamine receptor blocking properties, and therefore, spiperone derivatives with immunosuppressive effect yet without neuroleptic effect can be provided by the method of selection disclosed generally herein.

EXAMPLE 1

Inhibition of Induced Contact Hypersensitivity

Six-to-8-week-old female C57BL/6J or BALB/c mice were obtained from the Jackson Laboratory, Bar Harbor, Me. or from Charles River Laboratories, Kingston Facility, Stoneridge, N.Y., respectively.

Spiperone, mianserin, trazadone, haloperidol and oxazolone were purchased from the Sigma Chemical Co. (St. Louis, Mo.).

Oxazolone-Induced Contact Hypersensitivity—Sensitization and challenge for contact hypersensitivity were performed as follows. The abdomens of the mice were shaved with electric clippers, 50 µl of a 4% (w/w) solution of oxazolone in 4:1 (v:v) acetone:olive oil were applied to the shaved abdomen, and 5 µl of the same solution were applied to each hind footpad. Five to eight days later, the mice were challenged for contact hypersensitivity by applying 10 µl of a 0.5% (w:w) solution of oxazolone in 4:1 (v:v) acetone:olive oil to both the inner and outer surface of the right ear of each mouse (in the case of mice treated systemically with spiperone) or to both ears (in the case of mice treated topically with spiperone).

Dinitrofluorobenzene-Induced Contact Hypersensitivity—Mice were treated in an identical manner as above, except that 0.2% (v:v) 1-fluoro-2,4-dinitrobenzene (DNFB) in acetone was used for both sensitization and elicitation of the contact hypersensitivity response.

Systemic Spiperone Treatment—One hour after the application of oxazolone for elicitation of contact hypersensitivity, mice were treated subcutaneously with spiperone (150 or 30 mg/kg body weight) in 0.1 ml of carrier (Cremophor EL, BASF, Parsippany, N.J.), or with 0.1 ml of carrier alone. In a separate experiment, mice were treated in a similar fashion with 40 mg/kg body weight of trazadone, mianserin, haloperidol, or spiperone in 0.1 ml olive oil or with olive oil alone.

Topical Spiperone Treatment—To test whether spiperone affected the sensitization phase of contact hypersensitivity, 50 µl of 0.08% spiperone in propylene glycol was applied to the shaved abdomens of the mice on days −2, −1, 0, 1 and 2, with the day of oxazalone sensitization being designated day 0. To test the effects of spiperone on the expression of contact hypersensitivity in mice already sensitized to oxazolone; mice were treated with spiperone topically at two hours before or one or twenty-two hours after challenge for contact hypersensitivity, by applying 10 µl of a solution of spiperone in vehicle to both sides of the right ear. In the case of oxazolone-sensitized mice treated one hour after challenge, a 4% (w/w) spiperone suspension in 4:1:5 absolute ethanol:propylene glycol:olive oil was used, while 0.13% (w/w) spiperone solution in Vehicle-N (Neutrogena Corp., Los Angeles, Calif.) was used at the other time points. In the case of the DNFB-sensitized mice, 0.5% (w/w) spiperone in absolute ethanol was used.

Evaluation of Ear Swelling Response—Immediately before and 24 or 46 hours after application of oxazolone or DNFB, ear thicknesses were determined with an engineer's micrometer. The increment (delta) in ear thickness (ear swelling) was calculated as the 24- or 46-hour value minus the baseline (pre-challenge) value and expressed in units of $10^{-2}$ mm. Mice were killed by cervical dislocation after the measurement of 24-hour ear thickness was obtained, and the ears were processed for histologic examination.

Figure 10:
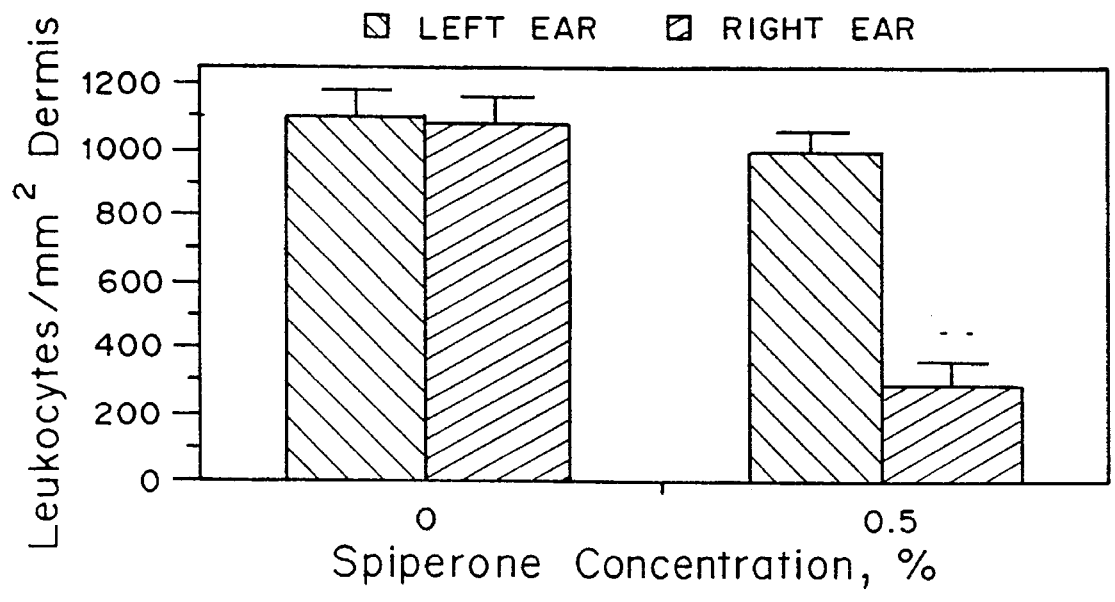
FIG. 10—Effect of topical treatment with spiperone on leukocyte infiltration associated with DNFB-induced contact hypersensitivity reactions. These data (mean ±SEM) are from the same mice whose ear thickness measurements are presented in FIG. 9. Topical treatment with spiperone significantly diminished the reactions when compared to those in vehicle-treated mice (**p<0.01). The slight effect of treatment of the right ears with spiperone on reactions expressed in the left ears of the same mice was not significant (p>0.05).

Quantification of Leukocyte Infiltration—In most experiments, both ears of each mouse were fixed in 4.0% buffered formalin and then processed routinely and embedded in paraffin for preparation of 6–7 μm-thick hematoxylin and eosin-stained sections. In some experiments (FIGS. 2 and 10), ears were fixed and processed into 1 μm thick, Epon-embedded, Giemsa-stained sections. All of the sections were coded and examined with an ocular grid at 400× under light microscopy by an observer unaware of the identity of the individual slides. The number of leukocytes/mm$^2$ of dermis was calculated by counting all of the leukocyte cells in an area of at least 0.14 mm$^2$ of dermis.

Statistical Analysis—Differences between groups were assessed by the 2-tailed Student's t test (paired for comparisons of left and right ears in the same mice, unpaired for comparisons between different groups of mice).

Results

Figure 2:
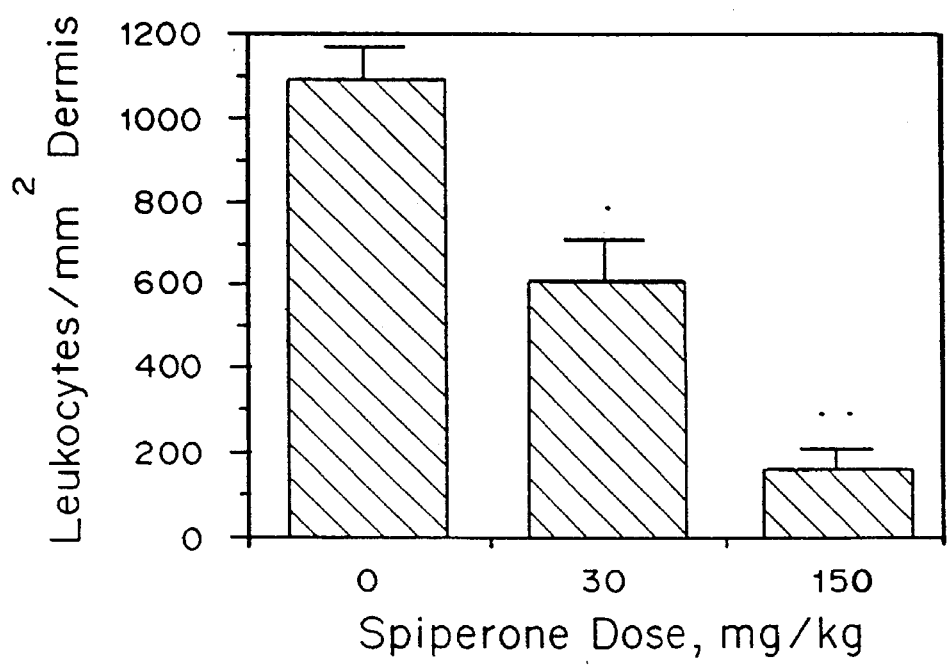
FIG. 2—Effect of systemic treatment with 30 or 150 mg/kg spiperone, subcutaneously, on leukocyte infiltration associated with 24-hour contact hypersensitivity reactions. These data (mean ±SEM) are derived from the same mice whose ear thickness values are shown in FIG. 1. The reduction in leukocyte infiltration observed in animals treated with 30 or 150 mg/kg spiperone was significant when compared to the reactions observed in animals treated with vehicle alone (* or **=$p<0.05$ or 0.01, respectively).

Effects of Systemic Treatment with Spiperone on Expression of Contact Hypersensitivity—The subcutaneous administration of spiperone at a dose of 150 mg/kg, 1 hour after challenge for contact hypersensitivity to oxazolone, markedly diminished (by 80%) the tissue swelling which developed in association with the contact hypersensitivity response (FIG. 1). FIG. 2 shows that the leukocyte infiltration associated with the response in mice treated with 150 mg/kg spiperone was also diminished by approximately the same amount (81% reduction compared to responses in mice not treated with the drug). However, at this dose, spiperone also produced other remarkable systemic effects. The mice rapidly became lethargic after administration of the drug, and, by 23 hours after spiperone injection, the mice exhibited profound depression of central nervous system function. They appeared to be in a deep sleep, neither ate nor drank, and responded weakly or not at all to touch. They did, however, exhibit responsiveness to pinch.

Some mice were treated with spiperone at 30 mg/kg subcutaneously (FIGS. 1 and 2). At this dose, spiperone diminished the tissue swelling associated with contact hypersensitivity to oxazolone to almost the same extent as did the higher dose (68% reduction with 30 mg/kg versus 80% reduction with 150 mg/kg) but reduced the leukocyte infiltration associated with the reaction by only 37% (FIG. 2). However, the central nervous system effects of spiperone at 30 mg/kg were substantially less pronounced that those observed at the higher dose. Thus, the mice treated with spiperone at 30 mg/kg were less sleepy than those treated with 150 mg/kg. However, the mice treated with 30 mg/kg appeared somewhat lethargic and were less interested in food and water than were control mice treated with carrier alone.

Figure 3:
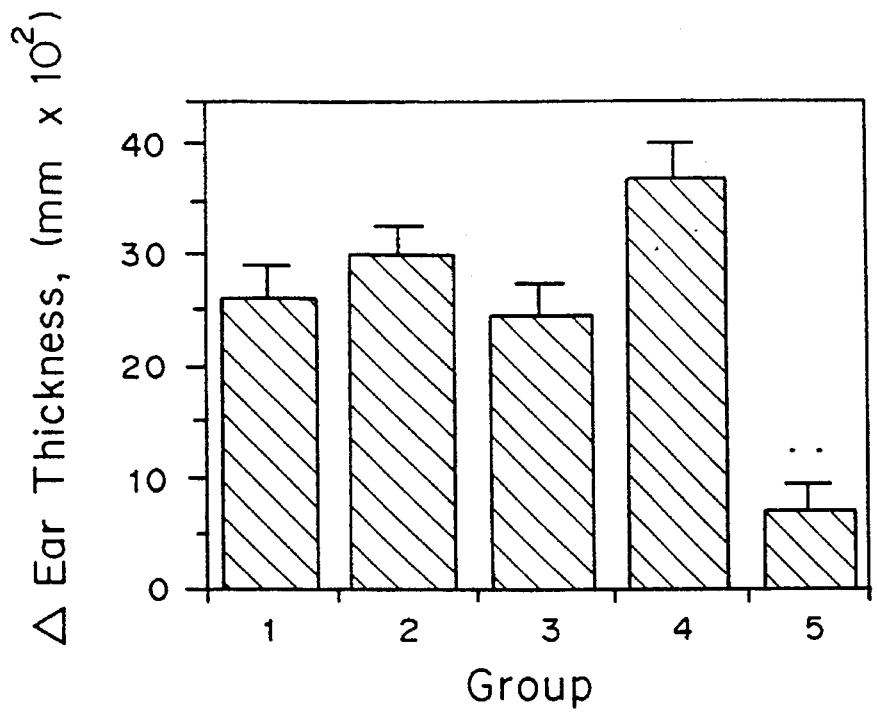
FIG. 3—Comparative effects of systemic vehicle (1), haloperidol (2), trazadone (3), mianserin (4) or spiperone (5) (all agents at 40 mg/kg, subcutaneously) on the tissue swelling associated with oxazolone-induced cutaneous contact hypersensitivity reactions. Spiperone, the other agents, or vehicle alone were administered to BALB/c mice 1 hour after challenge for contact hypersensitivity. The change in ear thickness (post-challenge value minus baseline pre-challenge value) was measured 24 hours after oxazolone challenge. The data are presented as the mean ±SEM. The reduction in ear swelling observed with spiperone was significant when compared to the reactions observed in the control, vehicle treated animals (**=$p<0.01$), whereas haloperidol, trazadone and mianserin did not significantly suppress the tissue swelling associated with contact hypersensitivity.
Figure 4:
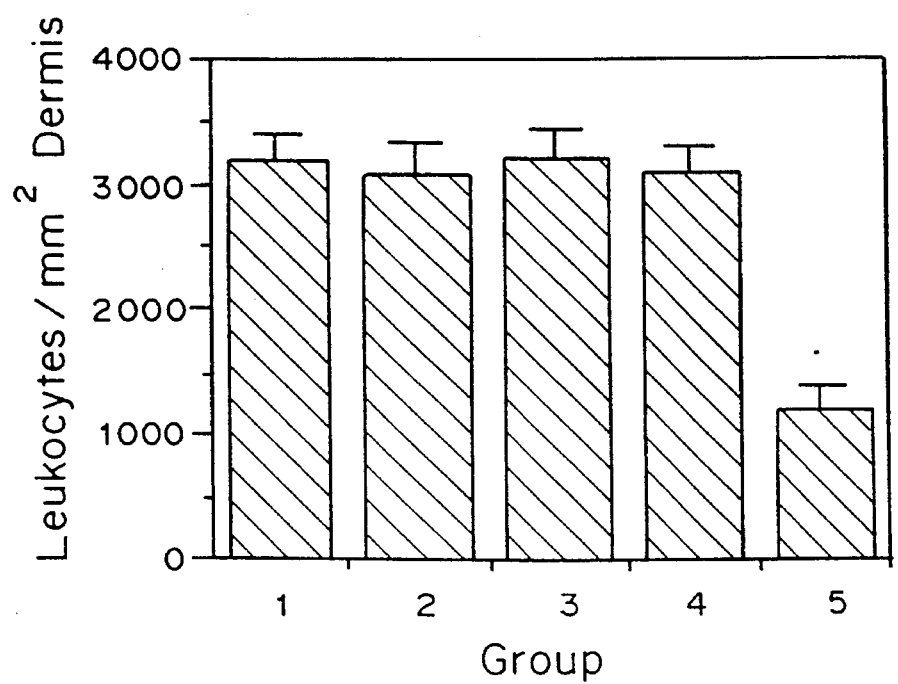
FIG. 4—Comparative effect of systemic treatment with vehicle (1) or haloperidol (2), trazadone (3), mianserin (4) or spiperone (5) (all agents at 40 mg/kg), administered subcutaneously, on leukocyte infiltration associated with 24-hour contact hypersensitivity reactions. These data (mean ±SEM) are derived from the same mice whose ear thickness values are shown in FIG. 3. The reduction in leukocyte infiltration observed in animals treated with spiperone was significant when compared to the reactions observed in animals treated with vehicle alone (*$p<0.05$), while haloperidol, trazadone and mianserin did not significantly suppress the leukocyte infiltration associated with contact hypersensitivity.

Systemic Spiperone Versus Other Serotonin or Dopamine Receptor Antagonists—In these experiments, systemic spiperone was compared to the serotonin receptor antagonists, trazadone or mianserin, and to the dopamine receptor antagonist, haloperidol, for their ability to inhibit cutaneous contact hypersensitivity. At a dose of 40 mg/kg, only systemic spiperone significantly reduced cutaneous contact hypersensitivity (FIG. 3, 4). The degree of lethargy in mice treated with 40 mg/kg of spiperone, trazadone, mianserin or haloperidol systemically (FIG. 1 and 2), appeared to be about the same as that in the mice treated with 30 mg/kg of spiperone systemically.

Systemic Spiperone Versus the Methyl Quaternary Ammonium Bromide Salt of Spiperone—In these experiments, systemically administered spiperone and systemically administered methyl quaternary ammonium bromide salt of spiperone were evaluated for their ability to inhibit cutaneous contact hypersensitivity. At systemic doses of 30 mg/kg, 15 mg/kg, 6 mg/kg and 1.5 mg/kg the spiperone methyl quaternary ammonium bromide salt produced significant suppression of the tissue swelling associated with oxazalone induced contact hypersensitivity, but with substantially less effect on the central nervous system (CNS) (FIG. 11) than spiperone. Similar results were obtained when the immune response was quantituted based on leukocyte infiltration, with doses of 15 mg/kg, 6 mg/kg, and 1.5 mg/kg of spiperone methyl quaternary ammonium bromide salt producing substantial suppression of the response, but with less CNS effects compared to spiperone given at the same dose (FIG. 12).

Figure 5:
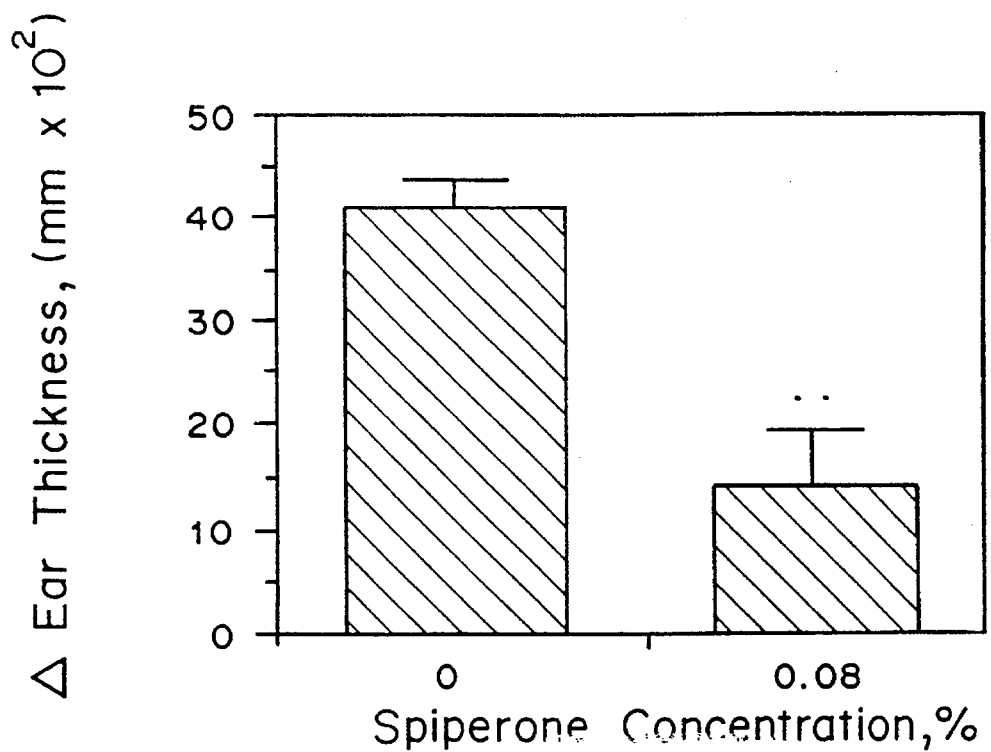
FIG. 5—Effect of spiperone applied topically during the period of sensitization on the tissue swelling associated with oxazolone-induced contact hypersensitivity reactions. Oxazolone was applied to the abdomens of BALB/c mice on day 0. The change in ear thickness was determined 24 hours after challenge with oxazolone on day 6. Treatment with spiperone (50 µl of 0.08% spiperone in propylene glycol) applied to the abdomens on days −2, −1, 0, 1 and 2 significantly diminished contact hypersensitivity reactions in the right ears of the treated animals (**$p<0.01$ when compared to the right ears in the control mice treated with vehicle).
Figure 6:
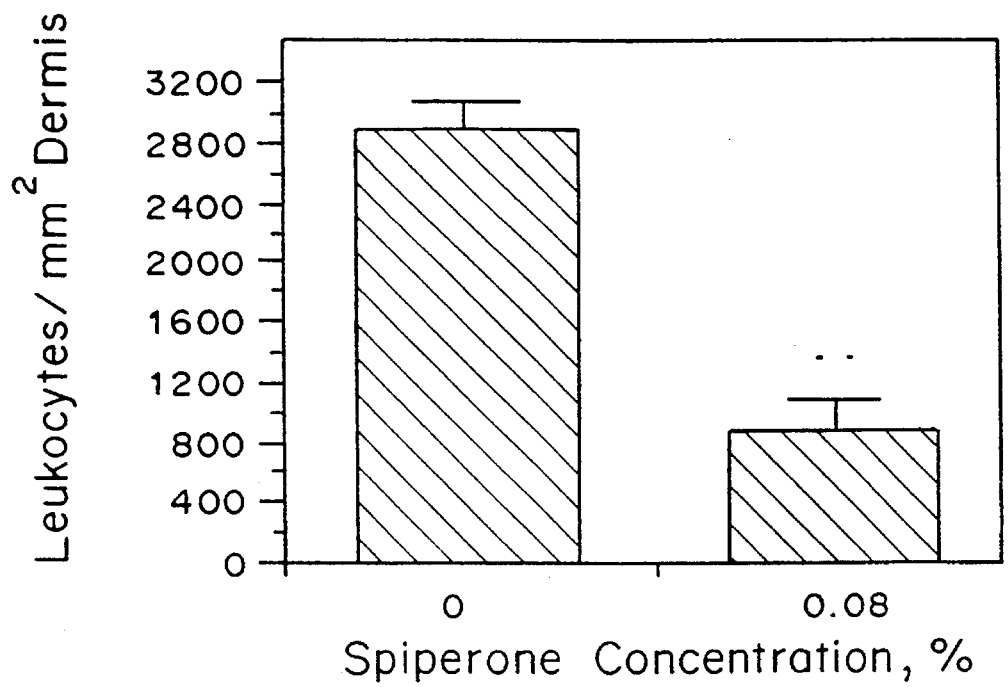
FIG. 6—Effect of spiperone applied topically during the period of sensitization on the leukocyte infiltration associated with oxazolone-induced contact hypersensitivity reactions. These data (mean ±SEM) are from the same mice whose ear thickness measurements are presented in FIG. 5. Topical treatment with spiperone significantly diminished the reactions when compared to those in vehicle-treated mice (**$p<0.01$).

Effects of Spiperone on the Sensitization Phase of Contact Hypersensitivity—For these experiments, mice were treated topically with spiperone in Vehicle-N or Vehicle-N alone, applied to the abdomen beginning two days prior to sensitization and continuing for a total of 5 days (FIGS. 5 and 6). Mice treated with spiperone exhibited 64% less tissue swelling and 70% less leukocyte infiltration at sites of hapten challenge than did vehicle-treated mice (p<0.01 for either comparison). These data show that treatment with topical spiperone can effectively inhibit the sensitization phase of cutaneous contact hypersensitivity.

Figure 7A:
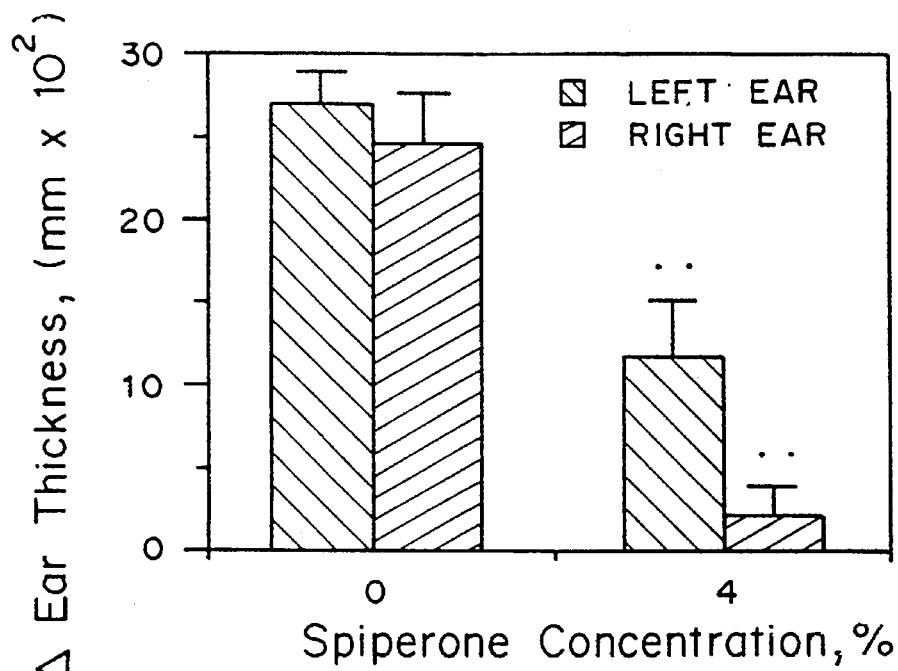
FIG. 7a,b,c—Effect of topically administered spiperone on tissue swelling associated with oxazolone-induced contact hypersensitivity reactions. Oxazolone was applied to both ears of all mice and the change in ear thickness was measured at a specified interval thereafter. a. One hour after oxazolone challenge, 4.0% spiperone in ethanol:propylene glycol:olive oil was applied to both surfaces of the right ears of some mice, whereas vehicle alone was applied to both surfaces of the right ears of the control (0% spiperone) mice. The ears were measured 24 hours after oxazolone challenge. Local treatment with 4% spiperone suppressed swelling in the treated ear (=$p<0.01$ vs either contralateral oxazolone treated ears or ears of vehicle treated group) and diminished the swelling in the contralateral ears (=$p<0.01$ vs left ears of vehicle treated group). b. Two hours before oxazolone challenge, 0.13% spiperone in Vehicle-N was applied to both surfaces of the right ears of some mice, whereas vehicle alone was applied to both surfaces of the ears of the control (0% spiperone) animals. The ears were measured 24 hours after oxazolone challenge. Local treatment of the right ear with spiperone significantly suppressed tissue swelling in the treated ear (**$p<0.01$ vs contralateral oxazolone treated ears or vs right ears of vehicle treated group). c. Twenty-two hours after oxazolone challenge, 0.13% spiperone in Vehicle-N was applied to both surfaces of the right ears of some mice, whereas vehicle alone was applied to both surfaces of the ears of control (0% spiperone) mice. The change in ear thickness was determined 24 hours after treatment with spiperone, i.e. at 46 hours after challenge with oxazolone. Treatment with spiperone significantly diminished contact hypersensitivity reactions in the right ears of the treated animals (*=p<0.01 when compared to the right ears in the control mice, and p<0.05 when compared to the contralateral ears of the same mice). The reactions in the left ears of the mice treated on the right ears with spiperone were also reduced when compared to reactions in the left ears of the vehicle-treated mice (p<0.01).
Figure 8A:
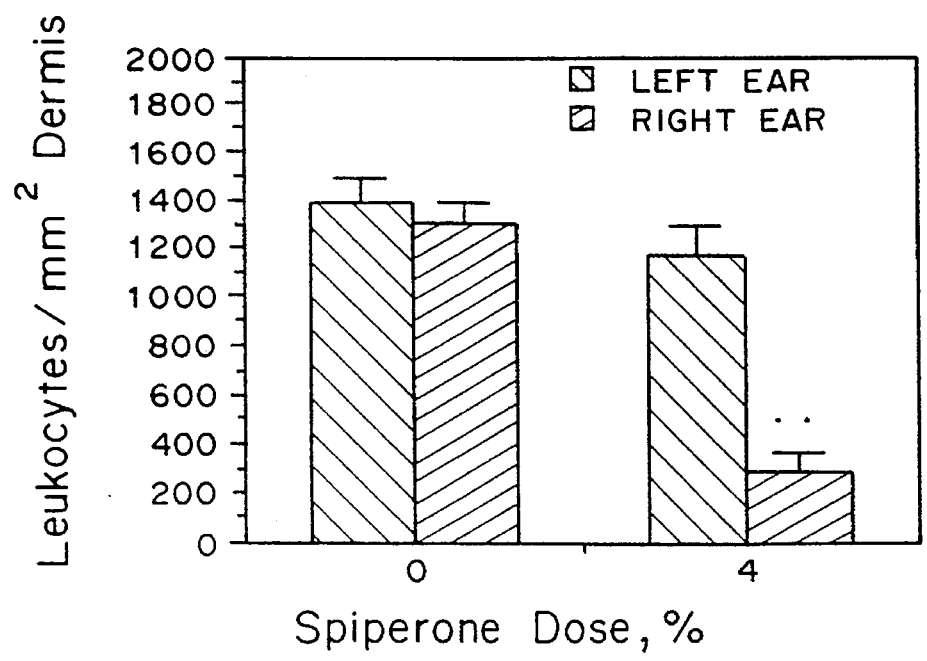
FIG. 8a,b,c—Effect of topical treatment with spiperone on leukocyte infiltration associated with oxazolone-induced contact hypersensitivity reactions. These data (mean ±SEM) are from the same mice whose ear thickness measurements are presented in FIG. 7a,b,c. Biopsies were performed 24 hours (a, b) or 46 hours (c) after application of oxazalone. Topical treatment with spiperone significantly diminished the reactions when compared to those in vehicle-treated mice (**=p<0.01).

Effects of Topical Spiperone on Expression of Contact Hypersensitivity—For these experiments, both ears of each mouse were challenged for elicitation of contact hypersensitivity by the application of oxazolone or DNFB (as appropriate) to both surfaces of both ears. Two hours before, one hour after or twenty-two hours after application of hapten, the right ears of some mice were treated with spiperone in vehicle, applied epicutaneously to both surfaces. The right ears of control mice were similarly treated, but with vehicle alone. Topical administration of a 4.0% suspension of spiperone in absolute ethanol, propylene glycol, and olive oil one hour after hapten challenge resulted in a marked diminution of the tissue swelling associated with contact hypersensitivity reactions elicited in the right (spiperone-treated) ear and had a smaller, but nonetheless significant, effect on the swelling associated with the contact hypersensitivity reaction elicited on the contralateral (untreated) ear (FIG. 7a). Thus, reactions in the untreated right ears were 90% smaller than reactions in the right ears of vehicle-treated mice, whereas reactions in the left ears of mice treated on the right ears with spiperone were reduced by 60% compared to the reactions in the right ears of the vehicle-treated mice (FIG. 7a). When the effect on leukocyte infiltration associated with the contact hypersensitivity reactions was assessed (FIG. 8a), the results were similar. Reactions in the spiperone-treated right ears were diminished by 76% compared to the right ears of vehicle-treated mice, whereas reactions in the left ears of mice treated on the right ears with spiperone were reduced only 22% compared to those in the left ears of vehicle-treated mice.

Figure 7B:
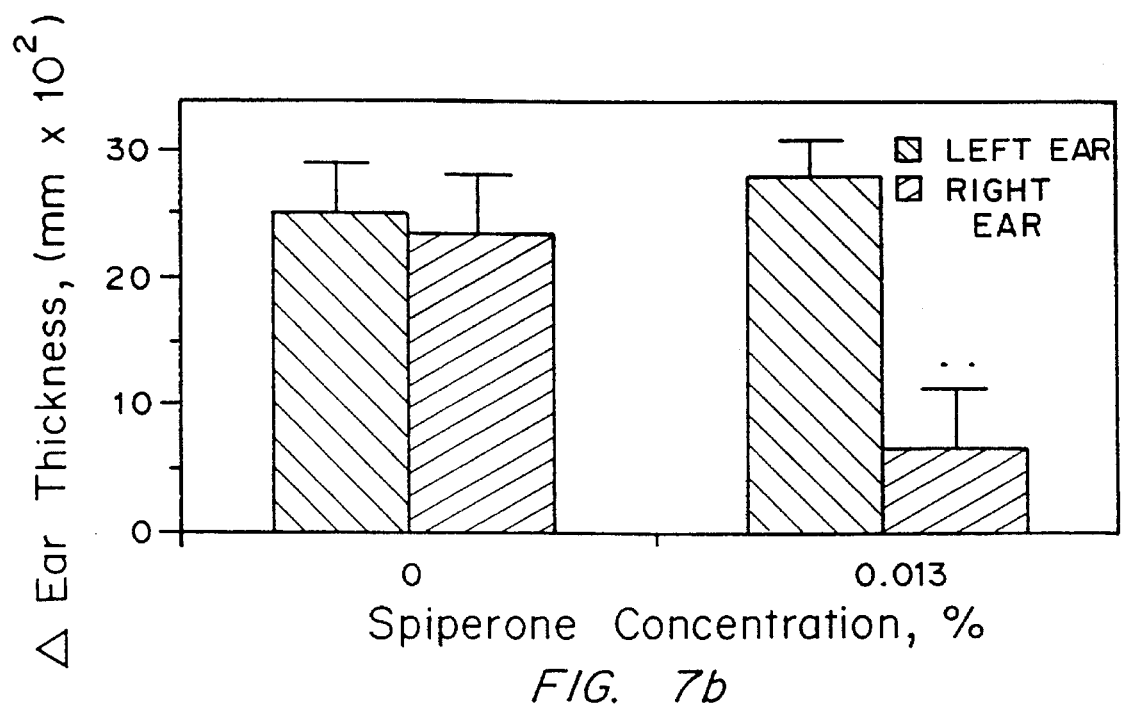
Figure 7C:
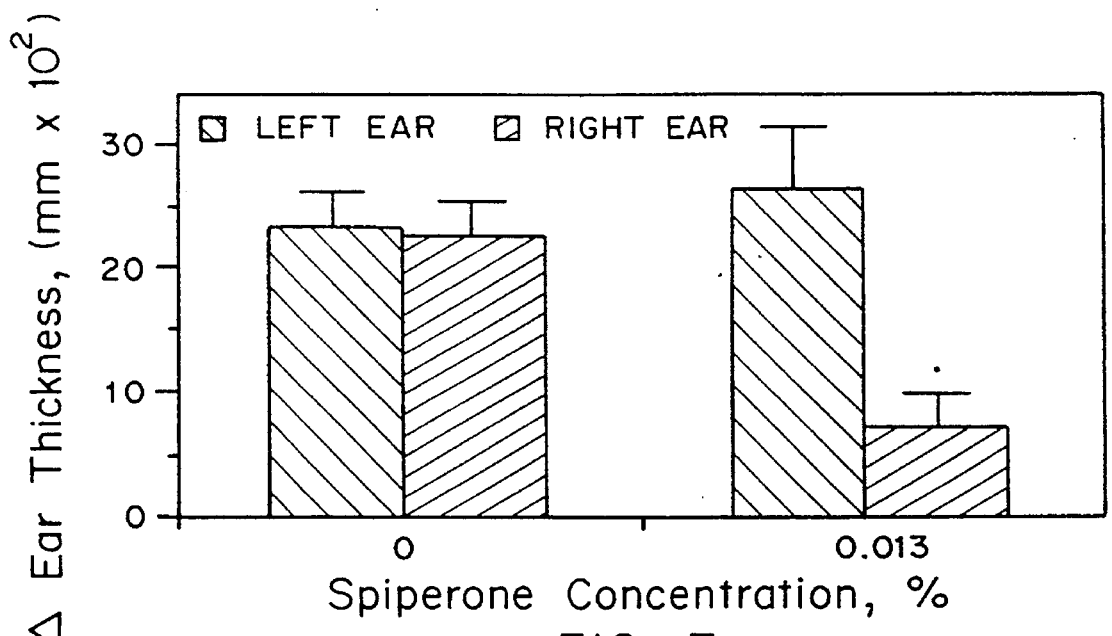
Figure 8B:
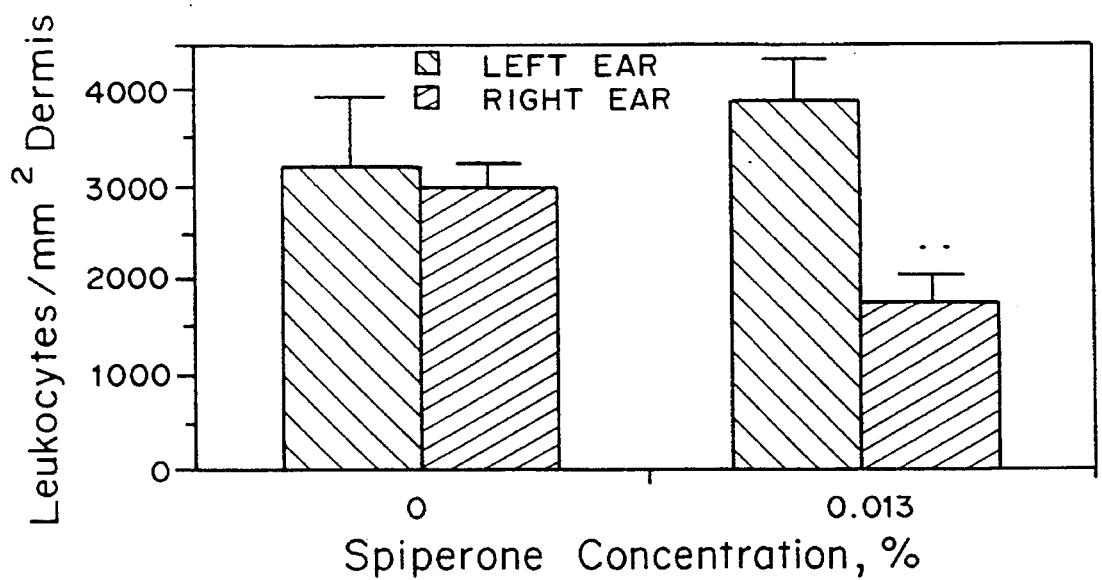
Figure 8C:
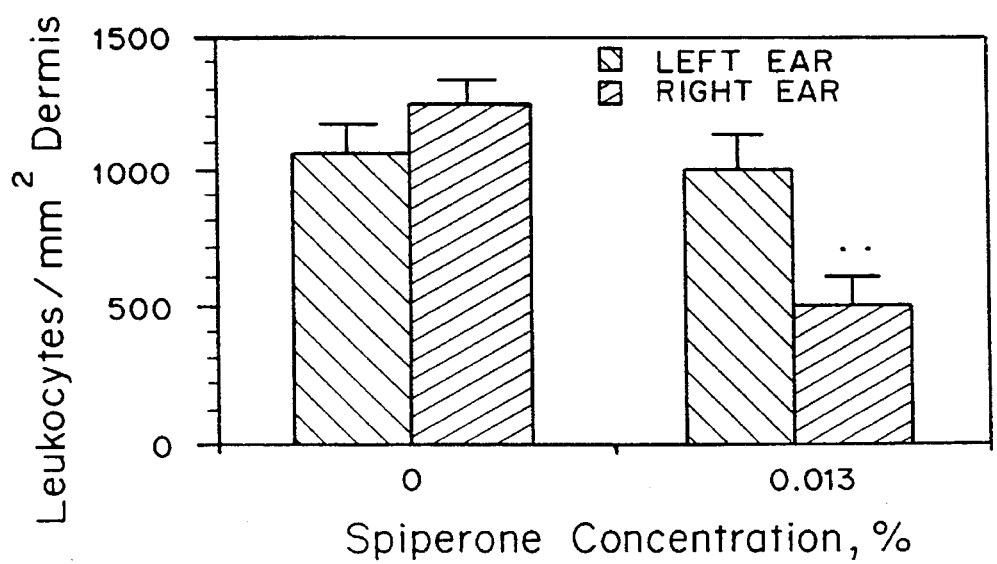

A lower concentration of spiperone (0.013%), applied topically to the right ear 2 hours before (FIG. 7b and 8b) or 22 hours after (FIGS. 7c and 8c) hapten challenge was also tested. The results demonstrate that the lower concentration of spiperone inhibited the majority of the tissue swelling and leukocyte infiltration associated with contact hypersensitivity reactions elicited at the site of treatment (the right ear), but had no significant effect on the intensity of the reactions elicited by the same dose of hapten applied to the contralateral (left) ear. Note that treatment with either vehicle had little or no effect on the responses (FIGS. 7 and 8).

Although topical application of spiperone was extremely effective in diminishing both the tissue swelling and the leukocyte infiltration associated with contact hypersensitivity reactions, these effects were observed in the absence of detectable alterations in the behavior of the mice. In contrast to mice treated systemically with spiperone, the mice treated topically with this agent appeared active and retained apparently normal interest in food and water.

Figure 9:
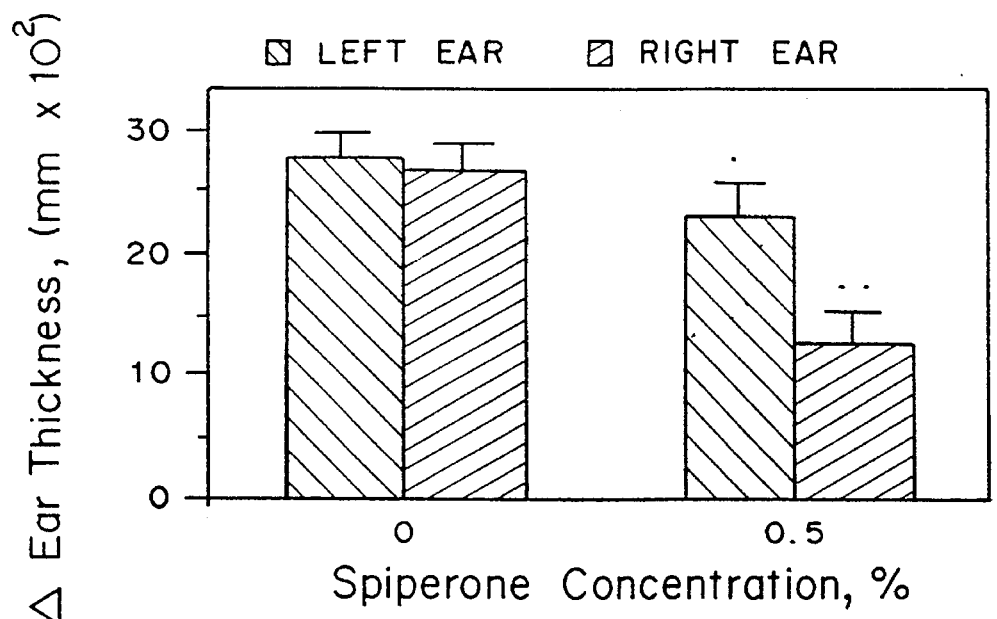
FIG. 9—Effect of topically administered spiperone on tissue swelling associated with DNFB-induced contact hypersensitivity reactions. DNFB was applied to both ears of C57BL/6J mice. One hour later, 0.5% spiperone was applied to both surfaces of the right ears of some mice, whereas vehicle alone was applied to both surfaces of the right ears of the control (0% spiperone) mice. The change in ear thickness was determined 24 hours after challenge with DNFB. Treatment with spiperone significantly diminished contact hypersensitivity reactions in the right ears of the treated animals (**p<0.01 when compared to the right ears in the control mice, and p<0.05 when compared to the contralateral ears of the same mice). The reactions in the left ears of the mice treated on the right ears with spiperone were also reduced slightly when compared to reactions in the left ears of the vehicle-treated mice (*p<0.05).

To evaluate the effect of topical treatment with spiperone on contact hypersensitivity reactions elicited with a different hapten, the effect of topical treatment with a 0.5% suspension of spiperone on the contact hypersensitivity reactions elicited with DNFB was examined. Topical treatment with spiperone significantly diminished the tissue swelling associated with reactions to DNFB (by 45%, FIG. 9) and had an even more significant effect on leukocyte infiltration (a reduction of 71% compared to right ears of vehicle-treated mice, FIG. 10). At this dose of spiperone and with this hapten, the effect of spiperone on reactions elicited in the left ears of mice treated on the right ears with the drug were modest (28% reduction in tissue swelling and 18% reduction in leukocyte infiltration compared to values for the left ears of vehicle-treated mice, FIG. 9 and 10). In fact, in this experiment, the effect of spiperone applied to the right ears on the leukocyte infiltration associated with reactions elicited in the left ears was not significant ($p > 0.05$).

EXAMPLE 2

Comparison of Immunosuppressant versus Anti-inflammatory Activity

Mice were sensitized to oxazolone as described in example 1. Three days later, slow release indomethacin pellets (0.05 mg, 3 week release) were implanted subcutaneously under light ether anesthesia. The dose of indomethacin delivered by these pellets has been previously shown to completely block prostaglandin synthesis in mice, by Jun, D. D., et al., *J. Invest. Dermatol.* 90:311 (1988).

Three days later, mice were challenged for contact hypersensitivity as in example 1. When the hypersensitivity response was assessed 24 hours later, indomethacin was shown to have no significant effect on the response. These data show that a classic anti-inflammatory agent, indomethacin, cannot suppress the immunologically specific oxazolone induced contact hypersensitivity response.

EXAMPLE 3

Evaluation of Serotonin Receptor Binding Activity or Dopamine Receptor Binding Activity of Spiperone Derivatives Spiperone derivatives which lack serotonin receptor binding or dopamine receptor binding activity can be identified as follows. A radiolabeled ligand known to bind serotonin and/or dopamine receptors can be bound to an appropriate substrate expressing one or both of these receptors. For example, radiolabeled quipazine which is available commercially can be used as the ligand. The spiperone derivative to be tested is then incubated with the radiolabeled quipazine ligand combination. Displacement of radiolabeled ligand is positive evidence that the spiperone derivative being tested can bind serotonin and/or dopamine receptors. The amount of radiolabeled ligand which is displaced is determined by an appropriate standard curve which can also provide information concerning binding affinities. The displaced radiolabeled ligand can be quantitated using a standard scintillation counter.

A detailed description of how to perform the binding studies using $^3$H-quipazine and the example follows:

Binding studies using $^3$H-quipazine are described in detail by Milburn, C. M. and Peroutka, S. J., *J. Neurochem.* 52:1787–1792 (1989). Briefly, rat cortices are homogenized in 20 volumes of 50 mM Tris HCl buffer pH 7.7 at 25° C. and centrifuged at 49,000×g for 10 min. The pellet is resuspended in fresh buffer and incubated at 37° C. for 10 min. After the final centrifugation, the pellet is resuspended in 80 volumes of Krebs-HEPES buffer (25 mM HEPES, 118 mM NaCl, 5 mM KCl, 2.5 mM $CaCl_2$, and 1.2 mM $MgCl_2$ pH adjusted to 7.4). Tissue (10 mg of original wet weight) is added to assay tubes containing 0.8 nM [$^3$H]quipazine and displacing drug or buffer in a final volume of 1 ml. Non-specific binding is defined using 1 micromole zacopride. After a 30 min incubation at room temperature, the tissue is rapidly filtered under vacuum through No. 32 glass fiber filters and rinsed twice with 5 ml of 50 mM Tris-HCl buffer pH 7.7. Radioactivity is quantified by liquid scintillation counting. All experiments are performed three to six times, each in triplicate. This same approach can be used with other radiolabeled ligands such as zacopride, granisetron, haloperidol, mianserin, ketanserin, 5-HT, dopamine, droperidol, or ritanserin.

Spiperone derivatives which have binding affinities for dopamine and/or serotonin receptors of one/tenth or less than native spiperone are considered to be potentially useful as systemic immunosuppressants if they are at least 50% as active as native spiperone on a weight basis in suppressing immunologically specific responses such as contact hypersensitivity.

EXAMPLE 4

Immunosuppressive and CNS Effect of the Methyl Quaternary Ammonium Salt of Spiperone The methyl quaternary ammonium bromide salt of spiperone was prepared by the following procedure. Spiperone (Sigma, 4.0 gm, 10 mmol) was dissolved in a 1:1 mixture of warm methylene chloride and methanol (80 mL). The solution was transferred to a Wheaton pressure bottle. Methyl bromide (2N in ether, 8 mL, 16 mmol) was added. The reaction vessel was heated in an oil bath at 60° C. overnight. The reaction solution was cooled and the white precipitate filtered, washed with methanol, and dried at high vacuum at room temperature. The product was obtained as a white solid (1.7 gm). Melting point, 245°–246.5° C.; elemental analysis (·1.25 H$_2$O): calc. C, 56.20; H, 6.19; N, 8.19; Br, 15.58. Found: C, 56.13; H, 6.14; N, 8.23; Br, 15.65.

FIGS. 11 and 12 illustrate the effect of spiperone and the methyl quaternary ammonium bromide salt of spiperone when injected intraperitoneally at different dosages on oxazolone induced contact hypersensitivity. The mice were injected with the test compound one hour after oxazolone challenge, and ear thickness measured at 24 hours after challenge. The dosages used are indicated in Table 1. The CNS effects were assessed by periodically observing the activity of the animals over a 23 hour period following injection of the test substance. The following scoring system was used and corresponded to the maximal effect observed during any observation period.

4+ Comatose
3+ Sleeping, but arousable
2+ Lethargic
1+ Less active than control
0 Normal

TABLE 1

| CNS Effect of Methyl Quaternary Ammonium Salt of Spiperone | | | |
|---|---|---|---|
| Group | Dose (mg/kg) | SPIP | QUAT |
| A | 30 | +++ | ++ |
| B | 15 | +++ | + |
| C | 6 | ++ | none |
| D | 1.5 | ++ | none |
| Control | 0 | none | none |

As indicated in FIGS. 11 and 12, the methyl quaternary ammonium bromide salt of spiperone significantly reduced ear swelling as compared to the control at dosages as low as 1.5 mg/kg, and had no appreciable CNS effect at dosages up to 6 mg/kg.

Modifications and variations of the present invention relating to compositions for the treatment of pathogenic immune responses that includes administering an effective amount of a spiperone derivative will be obvious to those skilled in the art from the foregoing detailed description of the invention. Such modifications and variations are intended to come within the scope of the appended claims.

We claim:

1. A method for treating a mammal in need of immunosuppression, comprising administering to the mammal an effective amount of a spiperone derivative of the formula:

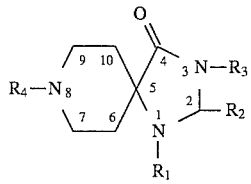

wherein:
R$_1$=H; alkyl, Y—CH$_2$(CH$_2$)$_n$— or Ar$_1$,
R$_2$=H or C$_1$ to C$_{20}$ alkyl;
R$_3$=H; alkyl,
CN(CH$_2$)$_2$—; X—(CH$_2$)$_n$—; X—(CH$_2$)$_n$CO—; NH$_2$C(NH)NHC(NH)(aryl)(CH$_2$)$_n$—; or X—(aryl)-(CH$_2$)$_n$—;
R$_4$=H, C$_6$H$_5$CH(CH$_2$CH$_3$)CH$_2$—, C$_6$H$_5$CH(CH$_3$)(CH$_2$)$_2$—, C$_6$H$_5$CH$_2$CH(CH$_3$)CH$_2$—, C$_6$H$_5$CH$_2$CH$_2$CH(CH$_3$)—, C$_6$H$_5$CH(CH$_3$)(CH$_2$)$_3$—, (2, 3, or 4)-(alkyl)—C$_6$H$_4$CH(CH$_3$)(CH$_2$)$_3$—, (2, 3, or 4)-(alkyloxy)—C$_6$H$_4$CH(CH$_3$)(CH$_2$)$_3$, C$_6$H$_5$CH(OCH$_3$)(CH$_2$)$_2$—,

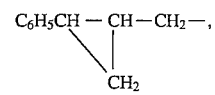

C$_6$H$_5$CO(CH$_2$)$_3$—, C$_6$H$_5$CO(CH$_2$)$_4$—, (2, 3, or 4)-(alkyl)—C$_6$H$_4$CO(CH$_2$)$_3$—, (2, 3, or 4)-(alkyloxy)—C$_6$H$_4$CO(CH$_2$)$_3$—, (2, 3, or 4)—X—C$_6$H$_4$-alkyl—(2, 3, or 4)—X—C$_6$H$_4$CO(CH$_2$)$_n$—, 2-thienyl—CO—(CH$_2$)$_3$—,

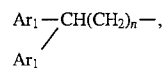

(2, 3, or 4)—X—C$_6$H$_4$C(CH$_3$)CH(CH$_2$)$_2$—, where the conformation about the double bond is cis or trans,
(2, 3, or 4)—X—C$_6$H$_4$C(CH$_3$)CHCH$_2$—, where the conformation about the double bond is cis or trans,
(2, 3, or 4)—X—C$_6$H$_4$COCH=CHCH$_2$—,
Y—CH$_2$(CH$_2$)$_n$—, Ar$_1$—(CH$_2$)$_n$—, C$_1$ to C$_{20}$ alkyl, X—(CH$_2$)$_n$CO—, or X—(CH$_2$)$_n$—;
n=1 to 6;
p is 1 to 20;
X=is independently F, Cl, Br, I, OCH$_3$, SO$_3$$^-$, NH$_2$, H, —OH, —COOH, —COOR, —SO$_3$H, —CN, —NHSO$_3$H, —NO$_2$, or —SO$_2$NH$_2$;
Y=H, F, Cl, Br, I, SO$_3$, —PO$_4$$^=$, —OH, —SH, —SCH$_3$, —CH$_3$SO$_2$$^-$, —NH$_2$, or —CO$_2$$^-$; and
Ar$_1$ is, independently, aryl, (2, 3, or 4—X—C$_6$H$_4$—), (2, 3, or 4)-(CH$_2$X)C$_6$H$_4$—, (2, 3, or 4)-(CX$_3$)C$_6$H$_4$—, (2, 3, or 4)-(CHX$_2$)C$_6$H$_4$—, 2-thienyl, or (2, 3, or 4)—X—C$_6$H$_4$CH$_2$—;

or its pharmaceutically acceptable salt, including a quaternary ammonium salt.

2. The method of claim 1, wherein the alkyl group is selected from the group consisting of cyclohexyl, (CH$_3$)$_2$CH—, (CH$_3$)$_2$CHCH$_2$—, CH$_3$CH$_2$CH(CH$_3$)—, (CH$_3$)$_3$C—, (CH$_3$)$_2$CH—, and CH$_3$(CH$_2$)$_n$—.

3. The method of claim 1, wherein the Ar$_1$ group is selected from the group consisting of C$_6$H$_5$—, (2, 3, or 4)-(OCH$_3$)C$_6$H$_4$— and (2, 3, or 4)-(CH$_3$)C$_6$H$_4$—; 2—X—C$_6$H$_4$—, 3—X—C$_6$H$_4$—, and 4—X—C$_6$H$_4$—.

4. The method of claim 1, wherein (2, 3, or 4)—X—C$_6$H$_4$-alkyl— is selected from the group consisting of (2, 3, or 4)—X—C$_6$H$_4$CH(CH$_2$CH$_3$)CH$_2$—, (2, 3, or 4)—X—C$_6$H$_4$CH(CH$_3$)(CH$_2$)—, (2, 3, or 4)—X—C$_6$H$_4$CH(CH$_3$)(CH$_2$)$_2$—, and (2, 3, or 4)—X—C$_6$H$_4$—CH(CH$_3$)(CH$_2$)$_3$—.

5. The method of claim 1, wherein the quaternary ammonium salt is of the formula —NR$^+$Z$^-$, wherein R is alkyl or benzyl, and Z is a counteranion.

6. The method of claim 5, wherein the counteranion is selected from the group consisting of chloride, bromide, iodide, —O-alkyl, toluenesulfonate, methylsulfonate, sulfonate, phosphate, and carboxylate.

7. The method of claim 6, wherein the carboxylate is selected from the group consisting of benzoate, succinate, acetate, propionate, glycolate, maleate, malate, citrate, tartrate, ascorbate, benzoate, cinnamoate, mandeloate, benzyloate, and diphenylacetate.

8. The method of claim 1 wherein the mammal is a human.

9. The method of claim 1, wherein the immune response is attributable disorder selected from the group consisting of autoimmune diseases, diseases of unknown etiology having an immunological component, and allergies.

10. The method of claim 1, wherein the mammal is treated for allograft rejection.

11. The method of claim 1, wherein the mammal is treated for a graft versus host disease associated with bone marrow transplant.

12. The method of claim 1, wherein the spiperone derivative is administered in a pharmaceutically acceptable carrier.

13. The method of claim 6 wherein the spiperone derivative in combination with an ophthalmic carrier is topically applied to the eye.

14. The method of claim 1, wherein the spiperone derivative is administered systemically.

15. The method of claim 8, wherein the dosage is between 0.1 mg/kg to 500 mg/kg of body weight per day as a single daily dose or divided daily doses.

16. The method of claim 1 wherein the spiperone derivative is administered in a time release formulation.

17. The method of claim 1 wherein the quaternary salt is prepared by combining spiperone or a spiperone derivative with a compound selected from the group consisting of: methyl chloride, methyl bromide, methyl iodide, methyl sulfate, methyl benzenesulfonate, methyl p-toluenesulfonate, ethyl chloride, ethyl bromide, ethyl iodide, n-propyl chloride, n-propyl bromide, n-butyl bromide, isobutyl bromide, sec-butyl bromide, n-amyl bromide, n-hexyl chloride, benzyl chloride, benzyl bromide, and ethyl sulfate.

18. The method of claim 1, wherein the spiperone derivative has decreased serotonin or dopamine receptor binding activity compared to native spiperone and which retains immunosuppressant activity.

19. The method of claim 1, wherein the spiperone derivative is a cycloamylose complex.

20. The method of claim 1, wherein the spiperone derivative is administered in combination with an antiviral.

21. A pharmaceutical composition comprising a quaternary ammonium salt of a spiperone derivative without significant neuroleptic effect of the formula:

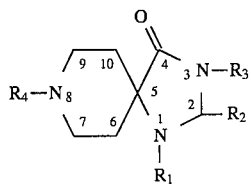

wherein $R_1$=H; alkyl, Y—$CH_2(CH_2)_n$— or $Ar_1$, $R_2$=H or $C_1$ to $C_{20}$ alkyl;

$R_3$=H; alkyl, $CN(CH_2)_2$—; X—$(CH_2)n$—; X—$(CH_2)_nCO$—; $NH_2C(NH)NHC(NH)(aryl)(CH_2)_n$—; or X—(aryl)-$(CH_2)n$—;

$R_4$=H, $C_6H_5CH(CH_2CH_3)CH_2$—, $C_6H_5CH(CH_3)(CH_2)_2$—, $C_6H_5CH_2CH(CH_3)CH_2$—, $C_6H_5CH_2CH_2CH(CH_3)$—, $C_6H_5CH(CH_3)(CH_2)_3$—, (2, 3, or 4)-(alkyl)-$C_6H_4CH(CH_3)(CH_2)_3$—, (2, 3, or 4)-(alkyloxy)-$C_6H_4CH(CH_3)(CH_2)_3$, $C_6H_5CH(OCH_3)(CH_2)_2$—,

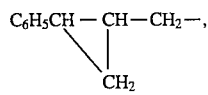

$C_6H_5CO(CH_2)_3$—, $C_6H_5CO(CH_2)_4$—, (2, 3, or 4)-(alkyl)-$C_6H_4CO(CH_2)_3$—, (2, 3, or 4)-(alkyl-oxy)-$C_6H_4CO(CH_2)_3$—, (2, 3, or 4)—X—$C_6H_4$-alkyl—(2, 3, or 4)—X—$C_6H_4CO(CH_2)_n$—, 2-thienyl—CO—$(CH_2)_3$—,

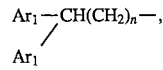

(2, 3, or 4)—X—$C_6H_4C(CH_3)CH(CH_2)_2$—, where the conformation about the double bond is cis or trans, (2, 3, or 4)—X—$C_6H_4C(CH_3)CHCH_2$—, where the conformation about the double bond is cis or trans, (2, 3, or 4)—X—$C_6H_4COCH=CHCH_2$—, Y—$CH_2(CH_2)_n$—, $Ar_1$—$(CH_2)_n$—, $C_1$ to $C_{20}$ alkyl, X—$(CH_2)_nCO$—, or X—$(CH_2)_n$—;

n=1 to 6;

p is 1 to 20;

X= is independently F, Cl, Br, I, $OCH_3$, $SO_3^-$, $NH_2$, H, —OH, —COOH, —COOR, —$SO_3H$, —CN, —$NHSO_3H$, —$NO_2$, or —$SO_2NH_2$;

Y=H, F, Cl, Br, I, —$SO_3$, —$PO_4^=$, —OH, —SH, —$SCH_3$, —$CH_3SO_2^-$, —$NH_2$, or —$CO_2^-$; and $Ar_1$ is, independently, aryl, (2, 3, or 4—X—$C_6H_4$—), (2, 3, or 4)-$(CH_2X)C_6H_4$—, (2, 3, or 4)-$(CX_3)C_6H_4$—, (2, 3, or 4)-$(CHX_2)C_6H_4$—, 2-thienyl, or (2, 3, or 4)—X—$C_6H_4CH_2$—;

in a pharmaceutically acceptable carrier.

22. The pharmaceutical composition of claim 21, wherein the alkyl group is selected from the group consisting of cyclohexyl, $(CH_3)_2CH$—, $(CH_3)_2CHCH_2$—, $CH_3CH_2CH(CH_3)$—, $(CH_3)_3C$—, $(CH_3)_2CH$—, and $CH_3(CH_2)_n$—.

23. The pharmaceutical composition of claim 21, wherein the $Ar_1$ group is selected from the group consisting of $C_6H_5$—, (2, 3, or 4)-$(OCH_3)C_6H_4$— and (2, 3, or 4)-$(CH_3)C_6H_4$—; 2—X—$C_6H_4$—, 3—X—$C_6H_4$—, and 4—X—$C_6H_4$—.

24. The pharmaceutical composition of claim 21, wherein (2, 3, or 4)—X—$C_6H_4$-alkyl— is selected from the group consisting of (2, 3, or 4)—X—$C_6H_4CH(CH_2CH_3)CH_2$—, (2, 3, or 4)—X—$C_6H_4CH(CH_3)(CH_2)$—, (2, 3, or 4)—X—$C_6H_4CH(CH_3)$ $(CH_2)_2$—, and (2, 3, or 4)—X—$C_6H_4$—$CH(CH_3)(CH_2)_3$—.

25. The pharmaceutical composition of claim 21, wherein the quaternary ammonium salt is of the formula —$NR^+Z^-$, wherein R is alkyl or benzyl, and Z is a counteranion.

26. The pharmaceutical composition of claim 25, wherein the counteranion is selected from the group consisting of chloride, bromide, iodide, —O-alkyl, toluenesulfonate, methylsulfonate, sulfonate, phosphate, and carboxylate.

27. The pharmaceutical composition of claim 26, wherein the carboxylate is selected from the group consisting of benzoate, succinate, acetate, glycolate, maleate, malate, citrate, tartrate, ascorbate, benzoate, cinnamoate, mandeloate, benzyloate, and diphenylacetate.

28. The pharmaceutical composition of claim 21 in a topical carrier in an amount by weight of between 0.001 and 100% spiperone derivative.

29. The composition of claim 21, wherein the spiperone derivative comprises spiperone complexed with a cycloamylose.

30. The composition of claim 21, wherein the spiperone derivative is in a time release formulation.

31. The composition of claim 21, wherein the spiperone derivative is administered in combination with a compound selected from the group consisting of antivirals, antifungals, antibiotics, antiinflammatories, and other immunosuppressants.

32. The composition of claim 21, wherein the spiperone derivative is provided as a quaternary salt.

33. The composition of claim 21, wherein the spiperone derivative has decreased serotonin or dopamine receptor binding as compared to native spiperone and which has immunosuppressant activity.

34. The composition of claim 21, wherein the quaternary salt is prepared by combining spiperone or its derivative with a compound selected from the group consisting of methyl chloride, methyl bromide, methyl iodide, methyl sulfate, methyl benzenesulfonate, methyl p-toluenesulfonate, ethyl chloride, ethyl bromide, ethyl iodide, n-propyl chloride, n-propyl bromide, n-butyl bromide, isobutyl bromide, sec-butyl bromide, n-amyl bromide, n-hexyl chloride, benzyl chloride, benzyl bromide, and ethyl sulfate.

35. The method of claim 1, wherein the spiperone derivative is administered in combination with an antifungal.

36. The method of claim 1, wherein the spiperone derivative is administered in combination with an antibiotic.

37. The method of claim 1, wherein the spiperone derivative is administered in combination with an antiinflammatory.

38. The method of claim 1, wherein the spiperone derivative is administered in combination with another immunosuppressant.

* * * * *